(12) United States Patent
Blumenfeld

(10) Patent No.: US 8,620,677 B2
(45) Date of Patent: Dec. 31, 2013

(54) ONLINE, INTERACTIVE EVALUATION OF RESEARCH PERFORMANCE

(75) Inventor: Tracy Harmon Blumenfeld, Haverford, PA (US)

(73) Assignee: PCRS, Inc., Wayne, PA (US)

( * ) Notice: Subject to any disclaimer, the term of this patent is extended or adjusted under 35 U.S.C. 154(b) by 1364 days.

(21) Appl. No.: 10/118,369

(22) Filed: Apr. 9, 2002

(65) Prior Publication Data

US 2003/0191664 A1    Oct. 9, 2003

(51) Int. Cl.
*G06Q 40/00*    (2012.01)

(52) U.S. Cl.
USPC ............................................................ 705/2

(58) Field of Classification Search
USPC ......................................................... 705/2, 3
See application file for complete search history.

(56) References Cited

U.S. PATENT DOCUMENTS

| | | | |
|---|---|---|---|
| 5,546,564 A | 8/1996 | Horie | 395/500 |
| 5,732,401 A | 3/1998 | Conway | 5/29 |
| 5,826,237 A | 10/1998 | Macrae et al. | 705/2 |
| 5,832,449 A | 11/1998 | Cunningham | 705/3 |
| 5,862,223 A | 1/1999 | Walker et al. | 380/25 |
| 5,893,081 A | 4/1999 | Poppen | 705/400 |
| 5,920,871 A | 7/1999 | Macri et al. | 707/104 |
| 6,037,940 A | 3/2000 | Schroeder et al. | 345/348 |
| 6,055,507 A | 4/2000 | Cunningham | 705/3 |
| 6,189,029 B1 | 2/2001 | Fuerst | 709/217 |
| 6,196,970 B1 | 3/2001 | Brown | 600/300 |
| 6,230,142 B1 | 5/2001 | Benigno et al. | 705/3 |
| 6,509,912 B1 * | 1/2003 | Moran et al. | 715/762 |
| 7,054,823 B1 | 5/2006 | Briegs et al. | |
| 7,076,439 B1 * | 7/2006 | Jaggi | 705/7.15 |
| 7,133,846 B1 * | 11/2006 | Ginter et al. | 705/54 |
| 7,711,580 B1 * | 5/2010 | Hudson | 705/3 |
| 2002/0016530 A1 | 2/2002 | Brown | 600/300 |
| 2002/0032581 A1 | 3/2002 | Reitberg | 705/2 |
| 2002/0087361 A1 * | 7/2002 | Benigno et al. | 705/3 |
| 2002/0099570 A1 * | 7/2002 | Knight | 705/2 |
| 2002/0169727 A1 | 11/2002 | Melnick et al. | 705/400 |

(Continued)

FOREIGN PATENT DOCUMENTS

| | | |
|---|---|---|
| EP | 1082693 A2 | 3/2001 |
| WO | 99/63473 A2 | 12/1999 |

(Continued)

OTHER PUBLICATIONS

McNair, C. J., Leibfried, Kathleen, H. J., "Benchmarking: A Tool for Continuous Improvement.", Oliver Wight Publications, Inc., 1992, chapters 4 and 7.*

(Continued)

*Primary Examiner* — Jason M Borlinghaus
*Assistant Examiner* — Martin Gottschalk
(74) *Attorney, Agent, or Firm* — Blank Rome LLP

(57) ABSTRACT

Medical and other research organizations, sites within those organizations, and physicians practicing at those sites register in an online database. The company providing the database posts a description of a clinical trial opportunity or other research opportunity. The company can search and match for physicians with research opportunities, or the physicians can browse the list of opportunities. Once it is determined who will perform the research and awarded a contract, performance data are collected at 30-day intervals over the life of the trial for computation of benchmarks. The benchmarks from one physician are compared anonymously to those from other physicians participating in the same opportunity.

12 Claims, 35 Drawing Sheets

(56) References Cited

U.S. PATENT DOCUMENTS

| | | | |
|---|---|---|---|
| 2003/0061096 A1 | 3/2003 | Gallivan et al. | 705/14 |
| 2003/0065669 A1* | 4/2003 | Kahn et al. | 707/100 |
| 2003/0130871 A1 | 7/2003 | Rao et al. | 705/2 |

FOREIGN PATENT DOCUMENTS

| | | |
|---|---|---|
| WO | 99/63473 A3 | 12/1999 |
| WO | 9963473 A2 | 12/1999 |
| WO | WO 01/29708 | 4/2001 |
| WO | 0155942 A1 | 8/2001 |
| WO | 01/93178 A2 | 12/2001 |
| WO | 01/93178 A3 | 12/2001 |
| WO | 02/15085 A1 | 2/2002 |

OTHER PUBLICATIONS

Re-Engineered to Capitalize on Advances in Technology, The Picas Database Has been internet Enabled and is now available on Fast•Track's Innovative Trialspace Platform, PICAS-e 2000-2002 Fast Track Systems, Inc.

Pharmaceutical Information Cost Assessment Service (a DataEdge Trial Space Product), http://www.fast-track.com/01products/products_picas.html.

A Database of actual unit Costs Drawn From Hundreds of Central Labe Contracts, Used for Budgeting and of Central Lab Expenses), http://www.fast-frack.com/01products/products_centralab.html, Sep. 30, 2002.

(4) four examples DataEdge, A Business Unit of Fast Track Systems Inc.

Fast Track's Protocol Quality Analysis Reduces Costly Amendments and Site Queries; ), http://www.fast-track.com/01products/products_protoqual.html, Sep. 30, 2002.

"Velos Launches Free Internet Clinical Research Service; Investigators at Top Medical Centers Sign Up," press release dated Oct. 4, 2001, © 2004, Velos, Inc., http://www.velos.com/velos/vellaunfrein.html.

"The Hub for Investigators: Finally, a Solution to End Clinical Trial Chaos," © 2000-2004, IntraLinks, Inc., http://www.intralinks.com/yb/lfsInve.asp.

Re-Engineered to Capitalize on Advances in Technology, The Picas Database Has been internet Enabled and is now available on Fast Track's Innovative Trialspace Platform, PICAS-e 2000-2002 Fast Track Systems, Inc.

Trialspace is an Innovative Technology Platform Combined with a Systems-Based Methodology which Yields an Integrated Trial . . . , http://www.fast-track.com/01products/products_overview.html, Sep. 30, 2002.

A Database of actual unit Costs Drawn From Hundreds of Central Labe Contracts, Used for Budgeting and Planning of Central Lab Expenses), http://www.fast-frack.com/01products/products_centralab.html, Sep. 30, 2002.

Fast Track's Protocol Quality Analysis Reduces Costly Amendments and Site Queries;), http://www.fast-track.com/01products/products_protoqual.html, Sep. 30, 2002.

* cited by examiner

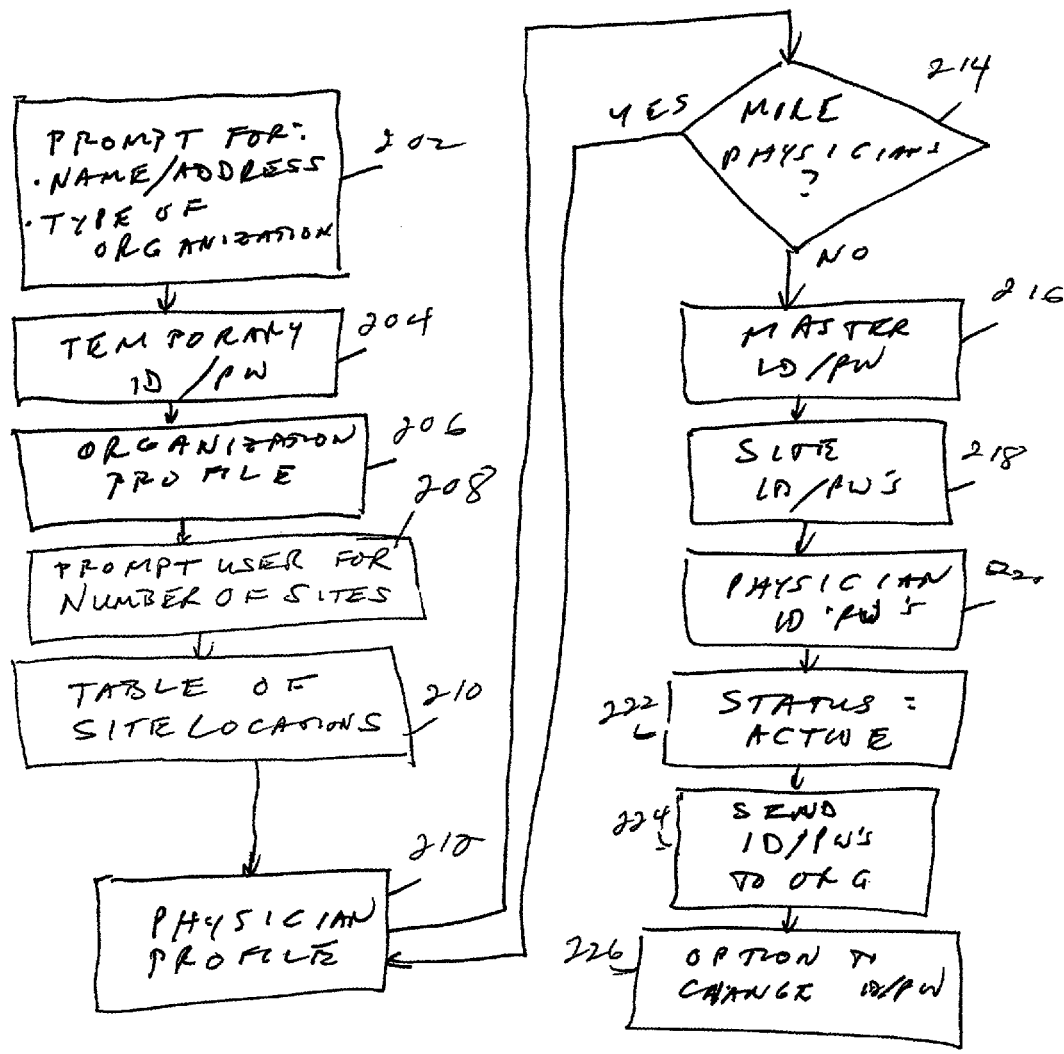

Figure 2A

PCRS Research Organization/Department Profile

Name Research Organization or Department

Change Password

Test

| Organization Contact Person: Last: | Test | First: | Test | MI: | | address-1 Test address-2 Test

City: Test   State: PA

Phone-area: 610   Phone: 9890660   Zip: 19097

Fax-area: 610   Fax Number: 9890660   E-mail: jo@rapidtrials.com

Total # Physicians: 2   Total # of States: 1   Total # of Locations: 3

(NEXT PAGE)

Figure 2C

Please give an address for all site locations (if different than above):

| Site Name | Address 1 | Address 2 | City | State | Zip | Delete |
|---|---|---|---|---|---|---|
|  |  |  |  | AE |  |  |
|  |  |  |  | AE |  |  |
|  |  |  |  | AE |  |  |

Is your organization currently involved in clinical research activities?  ○ Yes  ○ No How long has your organization been conducting clinical research? _____ years How many protocols have been coducted by this organization during the past 2 years? _____

Is the entire staff familiar with US FDA Regulatory Requirements and Good Clinical Practices in conducting a clinical trial?  ○ Yes  ○ No Are all of your PIs aware of the new requirements established by FDA regarding financial disclosure by clinical investigators (21 CFR part 54)?  ○ Yes  ○ No (NEXT PAGE)

Figure 2D

PCRS Physician Profile

Change Password

Name of Site/Institution or Organization: Test

Name of Site/Practice/Organization: Test Clinic

Name of Physician:

Last: Green    First: John

MI:    Degree: MD

Phone-area:    Phone:    E-mail:

Fax-area:    Fax Number:    Zip

City:    State: AE

Address ( if different than Site ):

address-1 address-2

License Number or Medical Authorization Number    State/Country

Figure 2E

REGISTRATION COMPLETE

ORGANIZATION REGISTRATION PROCESS GUIDE

As a member of the PCRS Network, you'll be able to use Rapidtrials.Com to submit for clinical trials online, access real-time data to measure your performance and more. Please take a few moments to provide us with the background information requested on the following pages.

As a member, you will have opportunities to update your site profile any time you access Rapidtrials.com Click on the links below to view and edit Profiles, or continue the registration process:

Test
    Test Clinic
        John Green
        Jane Smith
        Jack Bryer

Figure 2F

| Organization Name | Site Name | Physician Name | User ID | Password |
|---|---|---|---|---|
| Test | | | gone | gone |
| | Test Clinic | | XA17026 | 112431 |
| | | Jack Bryar | LA557 | 3558 |
| | | Jane Smith | QA510 | 3511 |
| | | John Green | KB400 | 3401 |

Figure 2G

PCRS Research Organization/Department Profile

Name Research Organization or Department

Test

Organization Contact Person Last: Test  First: Test  MI:

address-1: Test
address-2: Test
City: Test  State: PA
Phone-area: 610  Phone: 9890660  Zip: 19087
Fax-area: 610  Fax Number: 9890660  E-mail: info@rapidtrials.cc
Total # Physicians: 1  Total # of States: 1  Total # of Locations: 1

Application amount payed?  ○ Waived  ● Amount
Membership status  Active  Generate PW

Figure 2H

Organization Registration Page

Name of Research Organization or Department

| Last | | * First | | * MI | |
|---|---|---|---|---|---|

Address-1 _____ *
Address-1 _____ *

City _____ * State [AE ▼] *

Phone-area ___ * Phone _____ * Zip _____ *
Fax-area ___ * Fax: _____ * E-mail _____ *

Total # of Physicians ___ * Total # of States ___ * Total # of Locations ___ *

[SAVE]

*Required Fields

Figure 3B

PCRS / Rapidtrials Physician Registration

Name of Practice/Institution

Practice/Institution Location

Last _____ * First _____ * MI _____

Degree [None] * State [AE] *

Phone-area _____ * Phone _____ * E-Mail _____ *

Fax-area _____ * Fax: _____ *

License Number or Medical Authorization:

DEA Number:

Expiry Date:

Please select at least one specialty below:

| Specialty | Board Certified | Eligible | Delete |
|---|---|---|---|
| | ☐ | ☐ | ☐ |
| | ☐ | ☐ | ☐ |
| | ☐ | ☐ | ☐ |
| | ☐ | ☐ | ☐ |
| | ☐ | ☐ | ☐ |

(SAVE)

*Required Fields

Figure 3C

| | | | | | | |
|---|---|---|---|---|---|---|
| address-2 | Test | | | | | |
| City: | Test | State: | PA | | | |
| Phone-area: | 610 | Phone | 9890660 | Zip: | 19087 | |
| Fax-area: | 610 | Fax Number: | 9890660 | E-mail: | info@rapidtrials.cc | |
| Total # Physicians | 1 | Total # of States | 1 | Total # of Locations | 3 | |

Application amount payed?  ○ Waived  ● Amount [ ]
Membership status  [Active ▼]  [Generate PW]

| | | | |
|---|---|---|---|
| Physician Number: | 7277-01423-1554-2542 | | |
| Name of Site/Institution or Organization: | Test | | |
| Name of Site/Practice/Organization: | Test Clinic | | |

Name of Physician:

| | | | | | |
|---|---|---|---|---|---|
| Last: | Byer | First: | Jack | | |
| MI: | | Degree | MD | | |
| Phone-area: | | Phone: | | E-mail: | |
| Fax-area: | | Fax Number: | | Zip | |
| City: | | State | AE | | |

Address ( if different than Site ):

address-1 address-2

License Number or Medical Authorization Number

State/Country

DEA Number          Exp

| Specialty | Board Certified | Eligible | Delete |
|---|---|---|---|
| Pediatric | | | |
| | | | |
| | | | |
| | | | |
| Other | | | |
| Explanation / Comment | | | |

(NEXT PAGE)  (MAIN PAGE)  (SAVE CHANGES & EXIT)

Figure 5A

| Have you acted as a principle investigator on a Clinical Trial? | ○ Yes ○ No |
|---|---|
| Total # of Yrs Exp: | |
| Total # of Protocols: | |
| Have you acted as a sub-investigator on a Clinical Trial? | ○ Yes ○ No |
| Total # of Yrs Exp: | |
| Total # of Protocols: | |

CTO Phase:
- I ☐
- II ☐
- III ☐
- IV ☐

Year of most recent clinical trial: ____
- # Pts contracted: ____
- # Pts enrolled: ____

(NEXT PAGE) (MAIN PAGE) (SAVE CHANGES & EXIT)

Recorded Search Pattern
[Select ▼] (LOAD) (NEW) (SAVE) (SAVE AS)

SEARCH
Enable Criteria | Value
☐ Organization Name | [_____] — 602
☐ Site Name | [_____] — 604
☐ Physician Name | [_____] — 606
☐ Physician City | [_____]
☐ Physician State | [AE ▼] — 610
☐ Membership Status | [All ▼]
☐ Region | [North East ▼] — 612    608

Type of Site (please check all that apply):
☐ [Hospital, Childrens ▼]
☐ [Hospital, Childrens ▼]
☐ [Hospital, Childrens ▼]
☐ [Hospital, Childrens ▼]
☐ [Hospital, Childrens ▼]

IRB Utilization
☐ Central ☐
☐ Local ☐

Clinical and Trial Experience:
Therapeutic Area | Indication | Enable Clinical Experience | Enable Filter | Number of Clinical Trials Investigator Specialty:
☑ [Internal Medicine ▼] — 614
☐ [Abdominal ▼]
☐ [Abdominal ▼]

616

Keyword Search
[A keyword can be entered here]
(FIND)

— 618
(FIND PHYSICIANS)

600

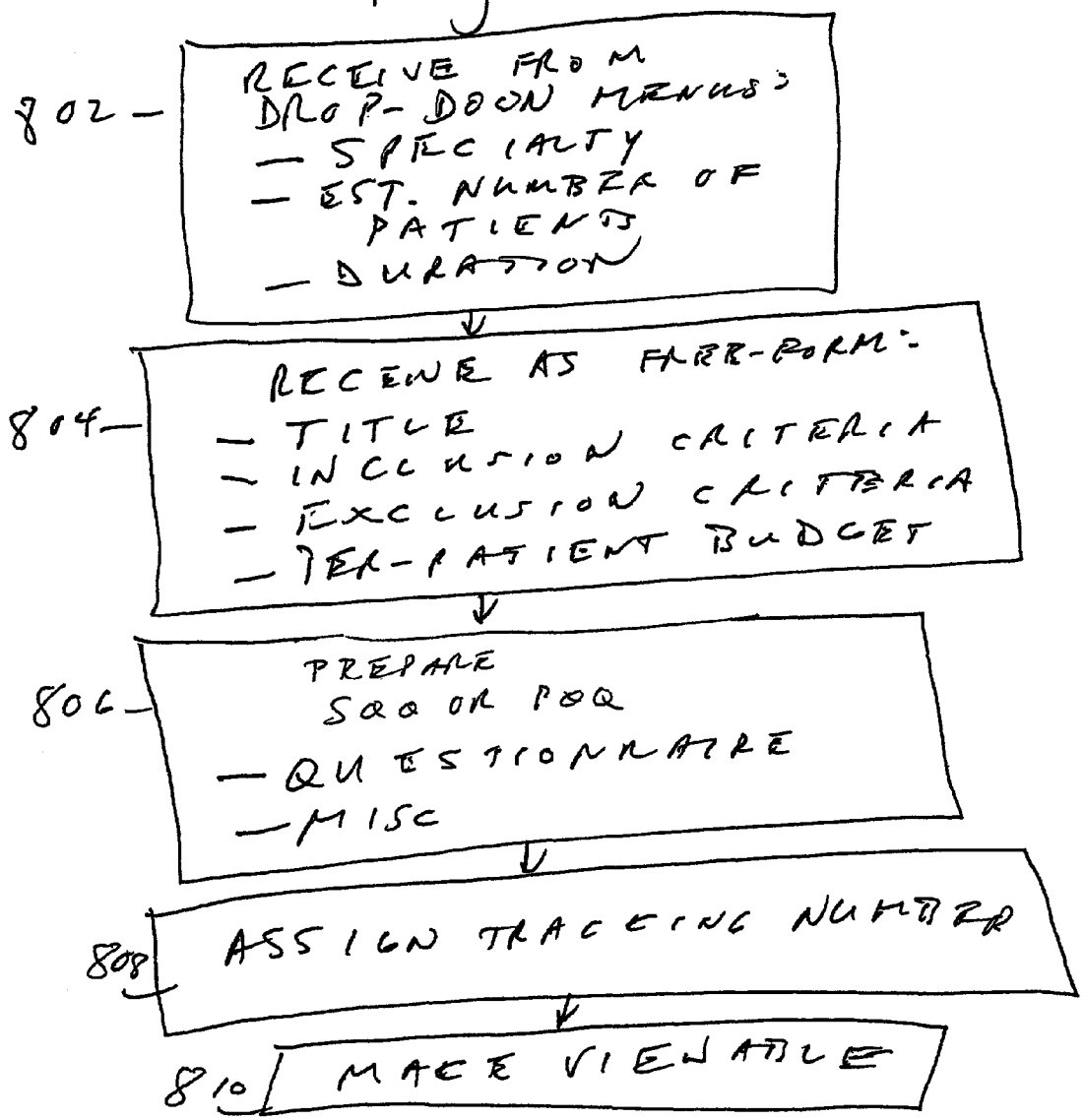

Figure 8A

Inpatient or Outpatient:
    Inpatient        □
    Outpatient       □

Key Inclusion Criteria:

Key Exclusion Criteria:

Removal of Patients from Therapy

Length of Enrollment Period (in months)  [____]

Expected Enrollment per site:            [____]

Duration of Therapy:                     [____]

Number of Patient Visits:                [____]

Investigators Meetings                   [____]

Anticipated Start Date:                  [____]

Special Request(s)/Equipment

Budget:                                  [____]

Extra Criteria #1
Description                              [____]

Extra Criteria #2
Description                              [____]

Extra Criteria #3
Description                              [____]

Extra Criteria #4
Description                              [____]

Figure 8B

SQQ DESIGN

| SQQ Standard Criteria | Del |
|---|---|
|  | ☐ |
| Type of Site (please check all that apply): | ☐ |
| Study Coordinator Experience | ☐ |
| Will the SC be available full-time to conduct this trial? | ☐ |
| Is the entire staff familiar with US FDA Regulatory Requirements and Good Clinical Practices in conducting a clinical trial? | ☐ |
| Are all of your PIs aware of the new requirements established by FDA regarding financial disclosure by clinical investigators (21 CFR part 54)? | ☐ |
| Have you / Has your site ever undergone an audit? | ☐ |
| IRB Utilization | ☐ |
| Who will be handling contracts? | ☐ |
| Where will payments be sent? | ☐ |
| Will the PI be available to attend the Investigators Meeting on date specified (if applicable) | ☐ |
| If no, then a sub-I? | ☐ |
| Name of study coordinator? | ☐ |
| How many patients do you see per year with this indication? | ☐ |
| Anticipated number of subjects enrolled per month in this trial: | ☐ |
| Performance Metrics (Please list your most recent trials): | ☐ |
| Are you currently involved in any other trials? | ☐ |
| If yes, please indicate how patient recruitment and resource allocation for this trial would not be affected? | ☐ |
| Where will the patients for this study be drawn from? | ☐ |
| What interests you about this trial? | ☐ |
| Comments about your site and your PI: | ☐ |

Figure 8C

| CTO Code | 437 |
| CTO Name | Test |
| Tracking# | 02-0555-03 | (SSS) view SSS Report | Recruiting |
| Post on Web | No | PCRS Project Manager | |

Figure 8D

| CTO Code | 437 |
| CTO Name | Test |
| Tracking# | 02-0555-03 | SSS | view SSS Report | Recruiting |
| Post on Web | | PCRS Project Manager | |

Figure 8E

INITIATION & ENROLLMENT
Date of Initiation Visit: _____ mm/dd/yy
Date Drug Received by site: _____ mm/dd/yy
Date first patient enrolled: _____ mm/dd/yy
Date of first monitoring Visit: _____ mm/dd/yy
Name of Monitor: _____
Company of Monitor: _____
Phone Number for Monitor: _____
Date of First payment to PCRS _____ mm/dd/yy Length of Enrollment Period (in months) _____
Enrollment Date _____ mm/dd/yy (NEXT PAGE)   Discard changes & Exit   Save changes & Exit

ENROLLMENT
30 Day Status Report

| | | |
|---|---|---|
| Number of Patients screened 30 days after initiation: | _____ | number of patients |
| Number of patients enrolled 30 days after initiation: | _____ | number of patients |
| Number of Dropouts by day 30 days after initiation: | _____ | number of patients |
| Number of Patients with Protocol violations | _____ | number of patients |
| Do you have 1 or more monitoring visits in the last 30 days? | ○ Yes ○ No | |
| Total number of patient charts reviewed | _____ | |
| Total number of queries identified by monitor | _____ | |

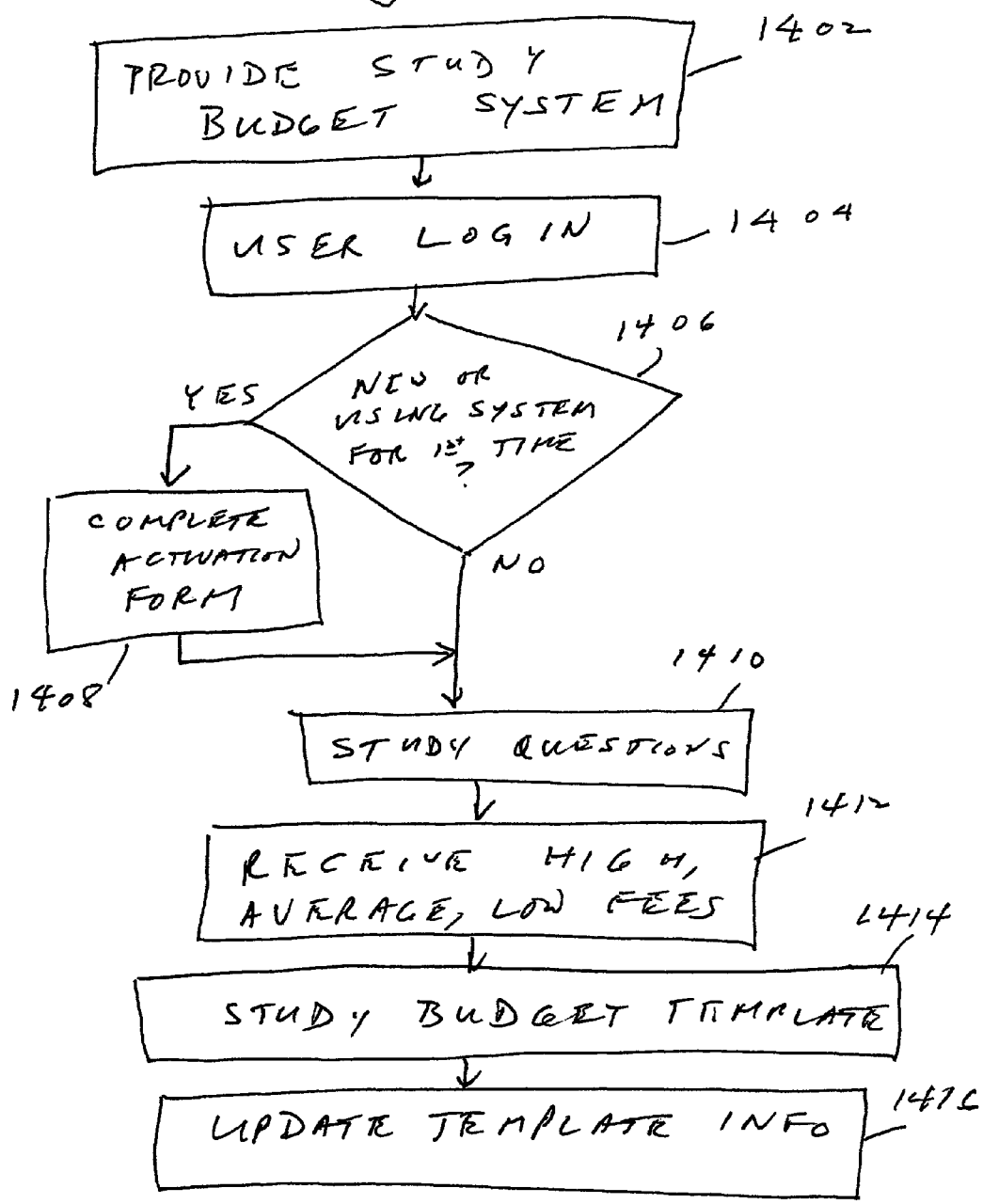

ONLINE, INTERACTIVE EVALUATION OF RESEARCH PERFORMANCE

FIELD OF THE INVENTION

The present invention is directed to a system and method for evaluation of the performance and progress of research trials and more specifically to such a system and method, which provide benchmark metrics in real time.

DESCRIPTION OF RELATED ART

In clinical trials for pharmaceuticals and the like, data must be taken over an extended period. For example, at intervals of time, typically 30 days, data must be taken on the number of patients who are participating in the trial, the number who have dropped out, the queries per patient, and the like.

However, the data are typically collected and tabulated by pharmaceutical companies to manage their project timeliness. Such information is rarely shared with the physicians and health-care professionals conducting the research studies for purposes of understanding how they are performing, how other research sites are doing and/or learning from other clinicians participating in the study about how to improve their study management and performance. Currently no electronic mechanism exists that systematically, and automatically provides clinicians the ability to interact with the physicians and health-care professionals conducting the research studies for purposes of understanding how they are performing, how other research sites are doing and or learning from other clinicians participating in the study about how to improve their study management and performance. Currently no electronic mechanism exists that systematically and automatically provides clinicians and/or pharmaceutical sponsors with the ability to obtain interactive, real-time benchmarks and with those benchmarks better assess physician capabilities for matching physicians and research sites and with those data better assess physician capabilities for matching physicians and research sites for future clinical trials.

One Internet-based technique for matching experts in the biological sciences with those needing their services is disclosed in WO 01/29708, published Apr. 26, 2001. That technique provides for matching based on qualifications and times of availability as well as payment. However, once the experts and their customers are matched, there is no evaluation of the work, which the former do for the latter.

SUMMARY AND OBJECTS OF THE INVENTION

It will be readily apparent from the above that a need exists in the art for an online, interactive evaluation of research performance. It is therefore a primary object of the invention to collect data concerning the progress of research and to provide an evaluation based on the collected data.

It is another object of the invention to provide an interactive, automated, online technique for doing so.

It is a further object of the invention to provide such an evaluation based on data collected at various time intervals.

It is a still further object of the invention to allow comparative evaluations among various trials.

It is a still further object of the invention to allow comparative evaluations without divulging the identity of one trial to researchers participating in another.

To achieve the above and other objects, the present invention is directed to an online, automated technique for collecting data not only for clinical trials but for other types of medical research including: marketing research, outcomes studies, disease management, etc. This type of medical research information would be information used to support the post approval product launches, marketing, product positioning, business development opportunities including licensing from clinical trials at intervals of, e.g., 30 days and for performing automated, online evaluations based on the data. The evaluations can be presented in textual or graphical formats. A common server can be used to collect data from multiple trials, with the appropriate protection of the data from each trial for privacy purposes. The comparisons, e.g., for cost per patient, can be presented anonymously; for example, the figures for the highest and lowest costs per patient can be given without identifying the sources for those figures.

Users register for the service as organizations. The system will then ask the user to register all sites and physicians that fall under the umbrella of the organization. If a physician is a solo practitioner, the physician still must complete all three profiles, although some information may be duplicated, since each profile focuses on collecting differing information. During the registration process, each user provides information to be entered into a database. For a physician, the information concerns the physician's own practice and the site, if any, at which the physician is an administrator. For a site, the information concerns such things as the facilities at the site and the physicians practicing at the site. For an organization, the information concerns such things as the type of organization and the sites and physicians within the organization.

A listing of a clinical trial opportunity (blinded synopsis) or other research opportunity (blinded synopsis) with an accompanying protocol synopsis specific questionnaire (SQQ) is posted on the website. The listing is categorized to allow browsing by prospective researchers who are members. In addition, the service can search the database to find suitable physicians, sites or organizations who preliminarily match the criteria the sponsor has provided to the service and then select which ones are to be contacted about the clinical trial opportunity. That occurs by cross-referencing project requirements with general information about the sites, physicians and organizations. Contacting members about opportunities occurs via e-mail or facsimile to invite them to consider the opportunity. Following the researchers' completion of any new data not currently in the database and contained in the SQQ, the research electronically submits the completed SQQ via email to the service. The service summarizes all the information across all completed SQQ's for the specific research opportunity and forwards qualified and matched researchers to the sponsor. The sponsor then selects which research provided by the service they will select for the clinical trial.

Once a researcher is selected for the study, information about the study is entered into the database, e.g., at the beginning and end of the study and at 30-day intervals or less therebetween. The information concerns such things as the number of patients who have signed up and the number who have dropped out. Thus, benchmarks can be computed over time.

Study (clinical trial/protocol) specific benchmarks from one researcher, site and or organization can be anonymously compared with those from other researchers, sites and/or organizations. In one example of a comparison, four values of a benchmark are given: the highest and lowest values from the researcher, site and organization participating in the study, the median from all researchers, sites and/or organizations, and the actual value from the researcher, site and/or organization with which the person viewing the results is linked in which the person viewing the results is participating. The identities of the other researchers, sites and/or organizations from which the information is provided are not given, thus preserving confidentiality. The user can thus see how their researcher, site and or organization performance results for the study compares with other researcher, site and/or organization performance results for the study and can use that information, e.g., to see where efficiency can be improved, budgets should be reallocated, patients that qualify for the study can be found, training is required or to make the case for an increase in the research budget.

BRIEF DESCRIPTION OF THE DRAWINGS

A preferred embodiment of the present invention will be set forth in detail with reference to the drawings, in which:

FIGS. 2, 2A-2I, 3, 3A-3D, 4 and 4A-4C show flow charts and screen shots of the registration and data inputting process for new users;

FIGS. 5A and 5B show a physician registration page;

FIG. 6 shows a search page;

FIG. 8 shows a flow chart of the processes involved in posting a CTO or ORO description;

FIGS. 8A-8E show screen shots of the processes of FIG. 8;

FIGS. 10 and 11 show pages used in collecting progress data;

FIG. 14 shows a flow chart of operation of an enhancement to the service which allows physicians to obtain information on fees.

DETAILED DESCRIPTION OF THE PREFERRED EMBODIMENT

Figure 1:
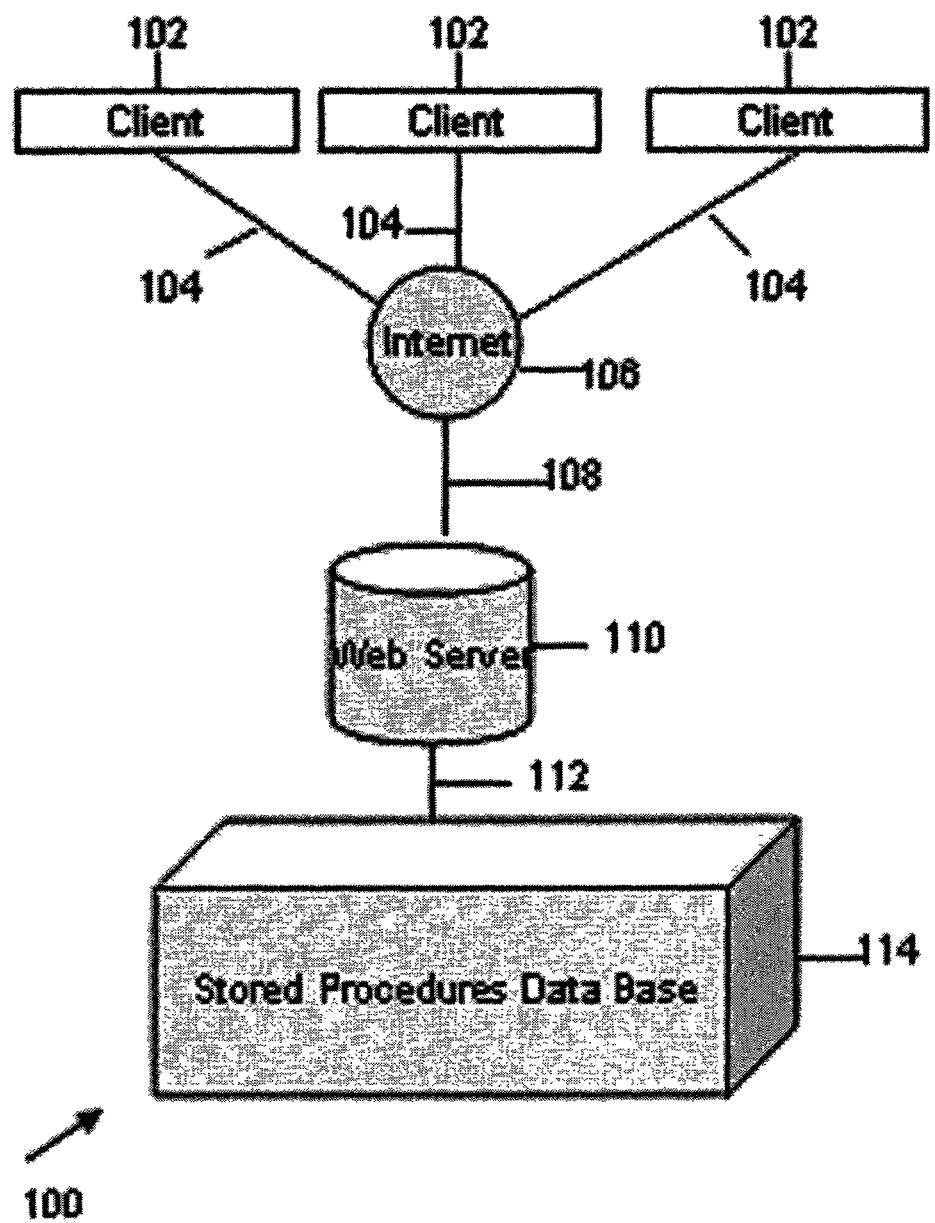
FIG. 1 shows a hardware architecture on which the preferred embodiment can be implemented.

A preferred embodiment of the present invention will now be set forth in detail with reference to the drawings, in which like reference numerals refer to like elements or process steps throughout.

FIG. 1 shows an example of a hardware architecture on which the preferred embodiment can be implemented. The design of the hardware architecture has been selected to follow the industry-standard N-tier architecture, separating site navigation and design from stored procedures and data. In that way, one part of the site can be redesigned without breaking another part of the site. For instance, the HTML which provides the user interface can be changed without affecting the stored procedures and tables of the database.

FIG. 1 shows such a hardware architecture 100. Client devices 102, which can be microcomputers or any other devices capable of communicating over the Internet, connect via any suitable connections 104, such as dial-up or cable modem connections, to the Internet 106, and thence via a full-time Internet connection 108 to a Web server 110. The client devices are used by physicians, research sponsors, research sites such as hospitals, and others participating in the operations of the preferred embodiment. The Web server 110 provides business services, such as site navigation and design, and is connected via a full-time dedicated connection 112 to a database server 114 storing the stored procedures and database tables. Thus, the client devices 102 access the stored procedures and database tables in the database server 114 only through the Web server 110. It is preferable to implement the Web server 110 and the database server 114 on separate, dedicated machines to facilitate backups and restarts with a minimum of disruption. The Web server 110 implements interactive HTML pages through known technologies, such as CGI or ASP. The database stored in the database server 114 is populated when physicians and organizations register and provide the information required for registration. As is known in the art, the Web server 110 provides persons accessing it from client devices 102 with several options, including physician registration and organization registration.

A user registers as an organization; physician registration and site registration are part of organizational registration. As noted above, a solo practitioner still registers as an organization. The organizational registration has two parts, the first part resulting in temporary status and the second part resulting in active status.

Figure 2A:
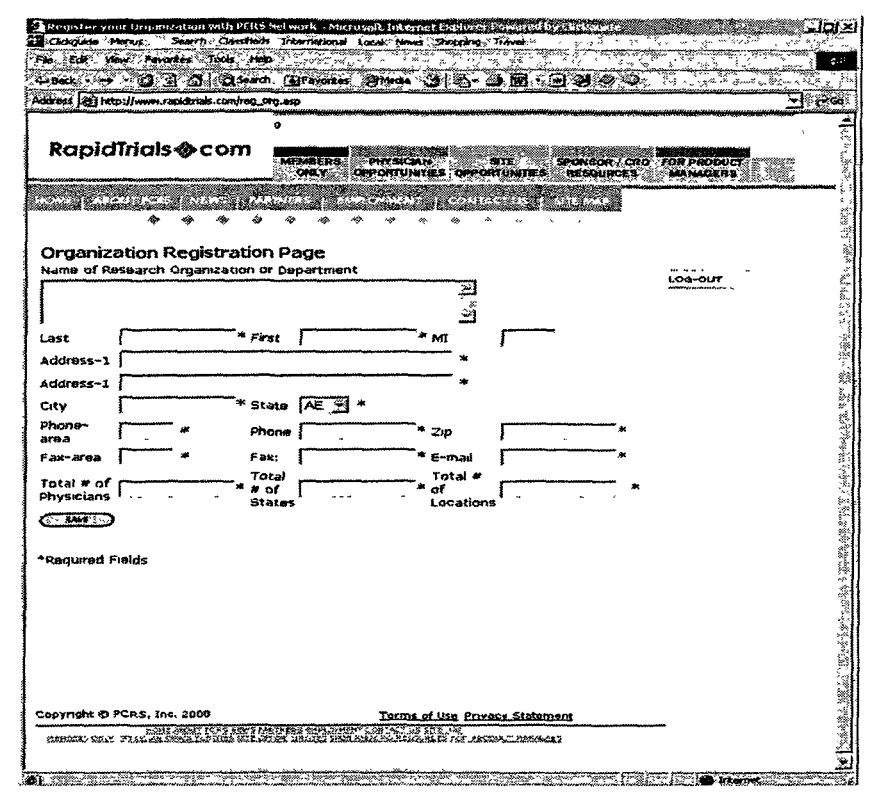
Figure 2B:
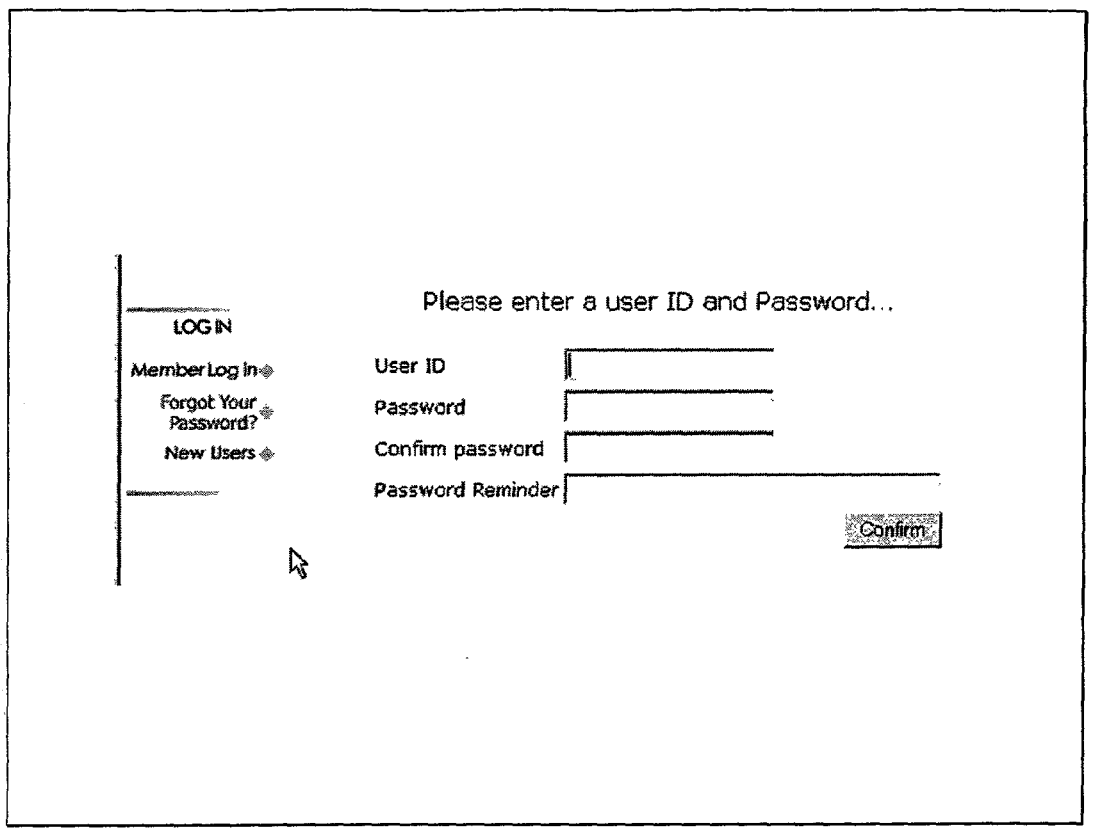
Figure 2I:
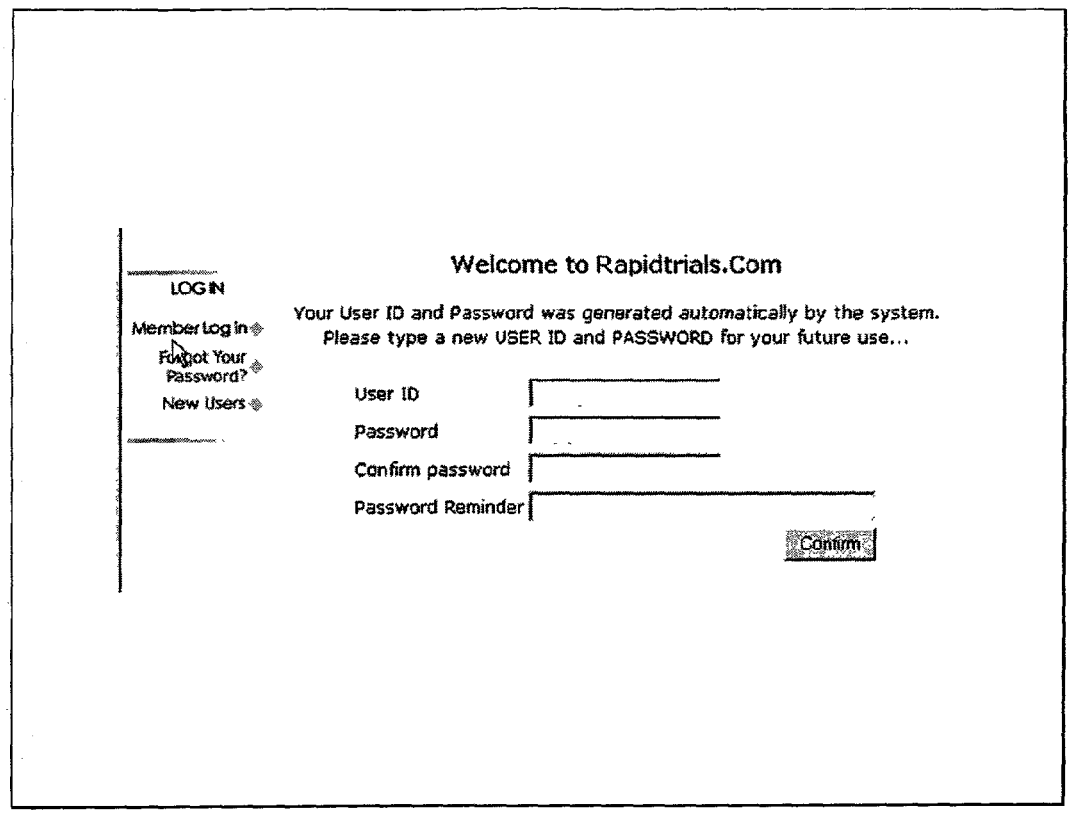

FIG. 2 shows an overview of organization registration. At step 202, the user is prompted for the name and address of the organization and for the type of organization (see the Web page of FIG. 2A). The latter is preferably selected through check boxes, so that multiple choices may be selected, although it may be selected through a drop-down menu or radio buttons if only one choice is allowed. At step 204, once that information is received, a temporary user identification and password are generated and provided to the user (or the user can select them; see FIG. 2B). The user is then allowed to view more detailed descriptions of the research opportunities; however, if any particular opportunity is selected, the user must proceed to the second part of the registration.

That second part begins at step 206, in which the user is prompted to complete an organizational profile (see FIG. 2C). When the User is completing the site location section of the organization profile, the first page of the organization profile asks "how many site locations" at step 208, and this automatically generates, at step 210, a table (see FIG. 2D) on page two of the organization profile with the necessary number of rows for all site locations. The User must complete this table in order to advance to page three of the organization profile; that will generate the correct number of site profiles. At step 212, the user completes a physician profile (see FIG. 2E) for each physician within the organization, until it is determined at step 214 (see FIG. 2F) that profiles have been completed for all physicians within the organization; step 214 can be performed like step 210. Identifications and passwords are generated for the organization as a whole, for each site, and for each physician at steps 216, 218 and 220, respectively (see FIG. 2G). At step 222, it is indicated in the database that the organization's status is that of an active member (see FIG. 2H). At step 224, the identifications and passwords are sent to the organization. At step 226, a responsible person at the organization has the option to change the identification and password for the organization (see FIG. 2I). The organization representative has the ability to change any data about the organization, sites or physicians and has complete access to all three profiles. The representative cannot add further sites or physicians or edit the name of a physician.

Figure 3:
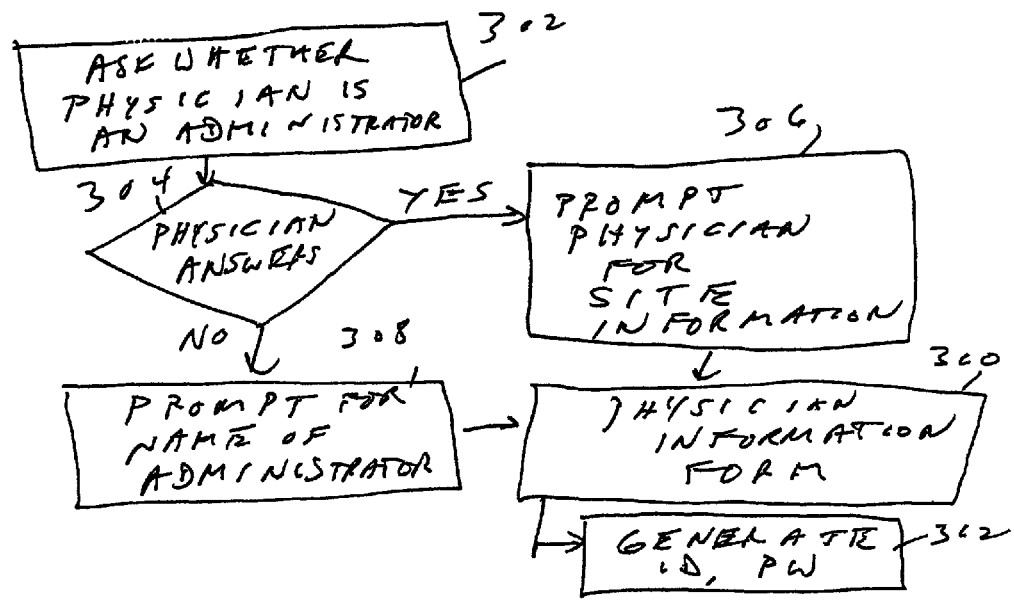
Figure 3A:
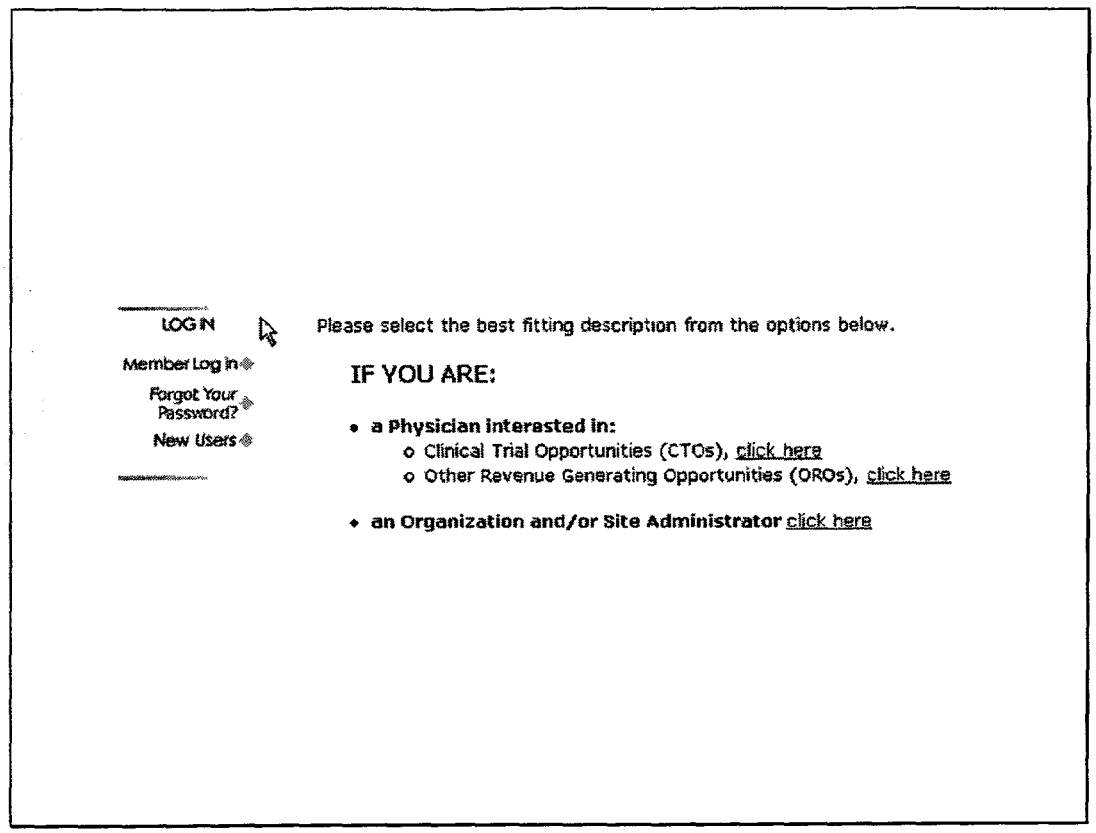

FIG. 3 shows an overview of the physician registration process of step 212. At step 302 (see FIG. 3A), the Web server asks whether the physician is an administrator at the site at which the physician works. If it is determined at step 304 that the physician has answered in the affirmative, the physician is prompted at step 306 (see FIG. 3B) for information about the site, in a manner which will be described in detail below. If not, the physician is prompted at step 308 for the name of an administrator at that site. Either way, the physician's information is taken in a physician information form at step 310

Figure 3D:

(see FIG. 3C). A user identification (ID) and password (PW) are generated for the physician at step 312 (see FIG. 3D).

Figure 4:
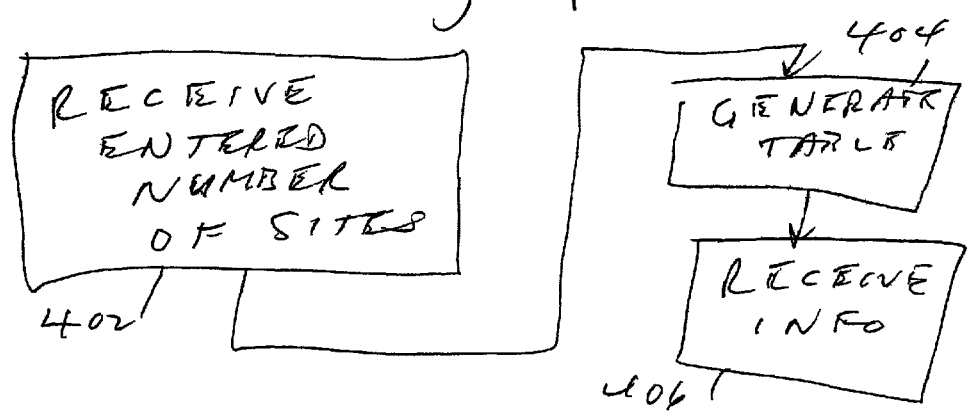
Figure 4B:
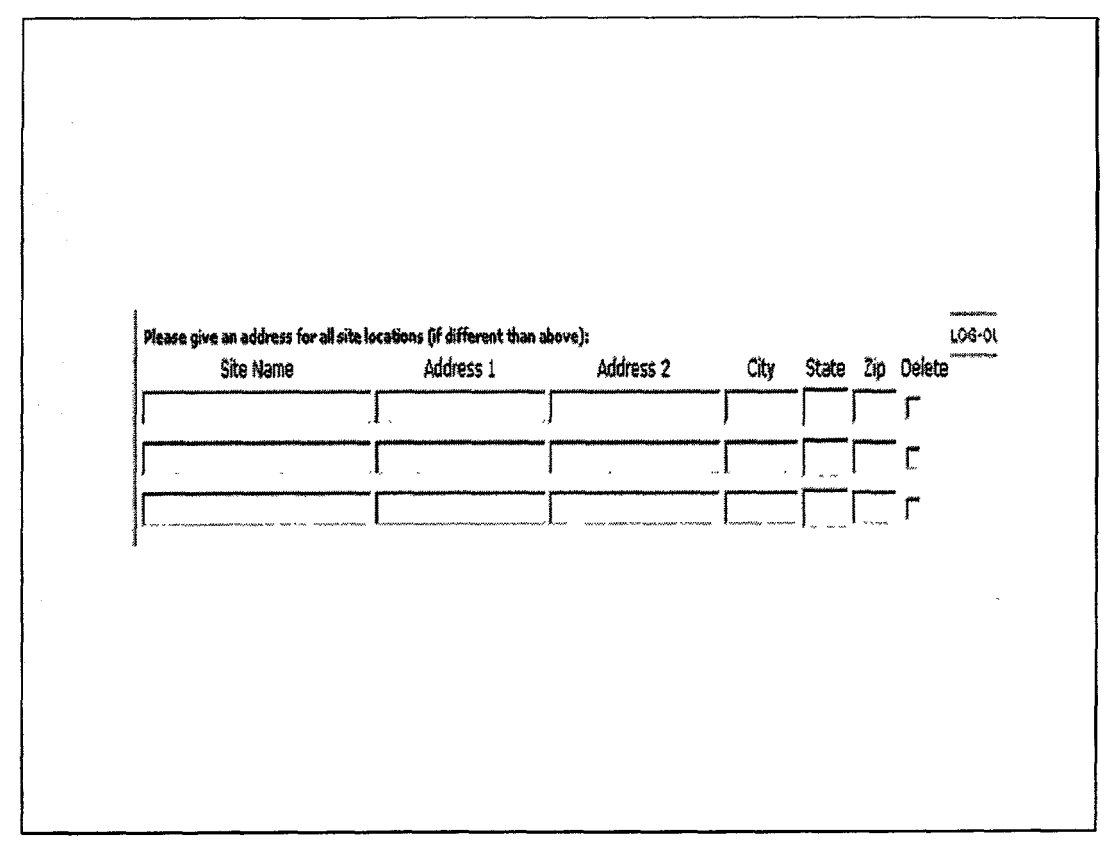
Figure 4C:
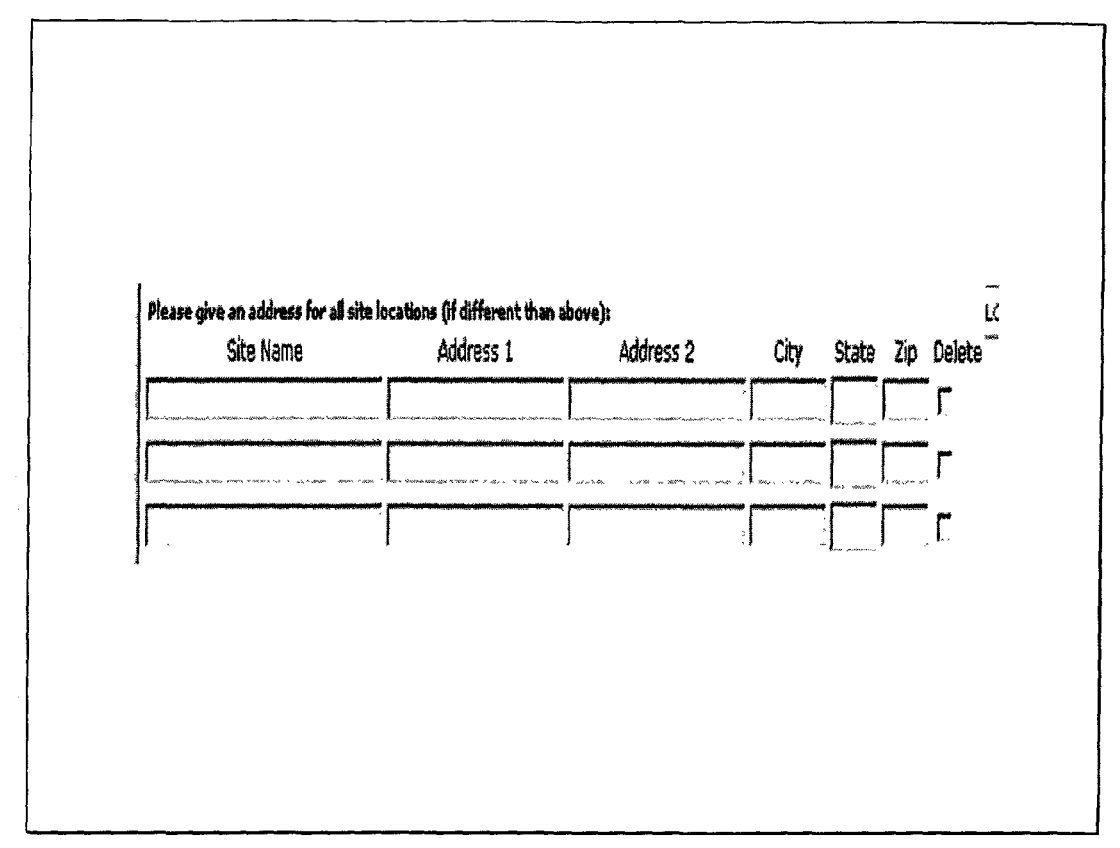

FIG. 4 shows an overview of the site registration of step 210. The number of sites input by the user is received at step 402 (see FIG. 4A). As noted above, a table of site locations, having a sufficient number of rows, is generated at step 404 (see FIG. 4B). The user completes the table, including information for each site, at step 406 (see FIG. 4C).

The data entry forms will now be described. In general, a data entry form can be implemented in HTML as one page or several; if it is implemented in several pages, each page ends with "Next Page" (or if the last page of the form "Submit"), "Discard Changes and Exit" or "Save Changes and Exit" options. Also, the same forms can be used to add information about new users and to update information for existing users.

FIG. 5A shows the first page of the physician's form. The first page 502 includes an area 504 for contact information, an area 506 for medical licensing and DEA information, and an area 508 in which the physician can identify specialties through drop-down menus. Other information, such as professional affiliations with one or more medical schools and hospitals, can be solicited here. There are also "Next Page" (or if the last page of the form "Submit"), "Main Page" and "Save Changes and Exit" buttons 510, 512 and 513, as mentioned above.

FIG. 5B shows a subsequent page 514 of the physician's form. As shown in FIG. 5B, the physician is asked about experience as a principal investigator in a clinical trial. Detailed experience on each clinical trial can be solicited in further pages, as well as information on any FDA or sponsor audit that the physician or the site has undergone, any administrative roles that the physician plays at the site, any articles or presentations in which the physician is named as an author, and any organizations and associations in which the physician is actively involved.

The pages requesting organization and site information are similar. In addition, the organization pages request the type of organization, while the site pages request what facilities the site has, among other things. Pages can also be provided to transfer a physician from one site or organization to another or to transfer a site from one organization to another. This function is accessible solely to employees of the service, not registered users.

The administrator of the database server 114 can accept the information as given or can take various steps to verify it. For example, the administrator can verify that a given facsimile number or e-mail address words, check a given medical license number, or interview either the person submitting the information or those persons named as references.

Once all of the data concerning participating physicians, organizations, and sites have been entered into the database, the database can be searched. FIG. 6 shows a search page for searching for physicians. The search page 600 uses text boxes and drop-down menus, although other suitable interface elements can be used as needed. In any text box, wildcard searching can be allowed.

Physicians can be searched by name, site, organization, or any combination of the three by use of the text boxes 602, 604, 606. The drop-down menu 608 allows the search to be conducted for physicians who are members, non-members, or either. The person conducting the search can select a state through a drop-down menu 610 or a region through a drop-down menu 612. A specialty can be selected through a drop-down menu 614. Key words can be entered in a text box 616. The page 600 can be designed to include any other search criteria, such as those relating to clinical trial experience.

Once all of the search criteria are entered, the user clicks on the "Find Physicians" button 618.

Figure 7:
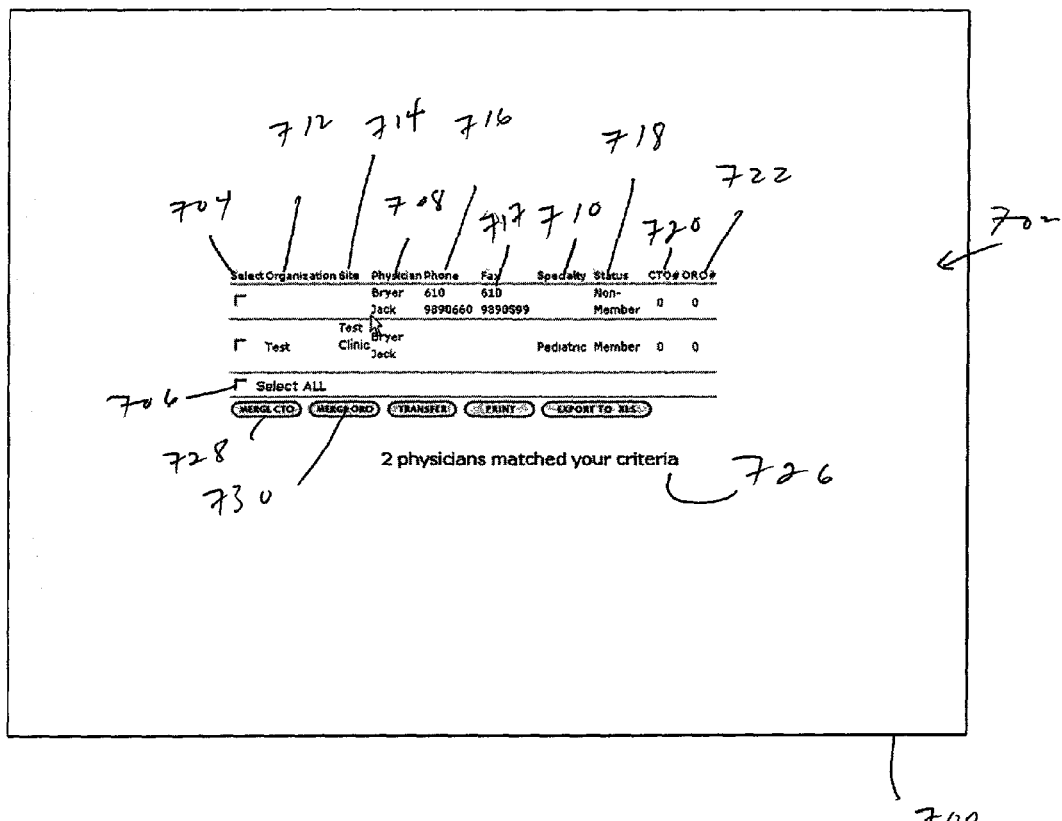
FIG. 7 shows a search result page.

Clicking on the "Find Physicians" button 618 causes the database server 114 to search for physician records matching the search criteria. The database server 114 passes the search results to the Web server 110 which formats them as shown in FIG. 7. The search results page 700 shows the search results in the form of a table 702. At the far left is a select column 704, which allows the user to select individual physicians for further consideration or to select all physicians through a "Select all" check box 706. The name column 708 lists the physicians by name, with links to their profiles in the database. The specialty column 710 gives each physician's specialty. The organization column 712 and the site column 714 identify the organization and site, respectively, with which each physician is associated and include links to those organizations' and sites' profiles. A telephone number column 716 and a facsimile number column 717 give that information for each physician. The membership status column 718 identifies each physician as a member or non-member. The CTO column 720 and the ORO column 722 list CTO's and ORO's, respectively, with which the physician is or has been involved. Columns can be sorted by clicking on the name of the column. An indicator 726 identifies the number of physicians who have matched the query. The merge buttons 728 and 730 allow the user to merge the records for the selected physicians with a CTO or ORO in a manner to be explained below.

Figure 8A:
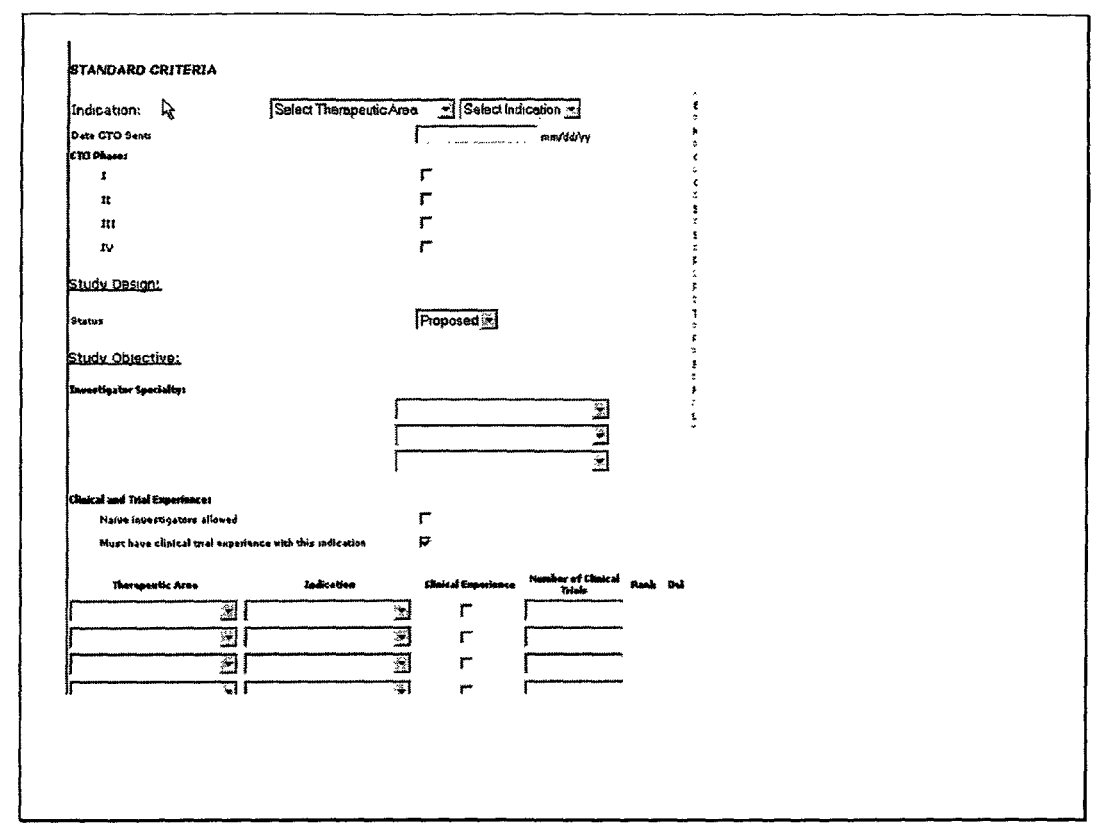

An employee of the service can enter a CTO or ORO as shown in FIG. 8. At step 802, the following are selected through drop-down menus or other suitable interface elements (see FIG. 8A): the specialty concerned (e.g., urology), the estimated number of patients, and the duration. At step 804, the following are input as free-form text (see FIG. 8B): a descriptive title of the study, one or more inclusion criteria for patients (e.g., male patient aged 40-85 years), one or more exclusion criteria for patients (e.g., no previous prostatic surgery within two weeks of base line), and a per-patient budget (this can be indicated as "to be negotiated"). The criteria can also be selected through drop-down menus, in which case there will be an option to add criteria not appearing in the menus. The criteria can also be assigned a sorting order. Through a Design SQQ/PQQ Interface, the relevant SQQ or PQQ is designed and posted on the web at step 806 (see FIG. 8C). A number is manually assigned at step 808 (see FIG. 8D). The opportunity can be made viewable to network members only by an employee of the service at step 810 (see FIG. 8E). The CTO or ORO can be made viewable to persons viewing the organization's or site's profile or in a list sorted by specialty; preferably, both are done.

Figure 9:
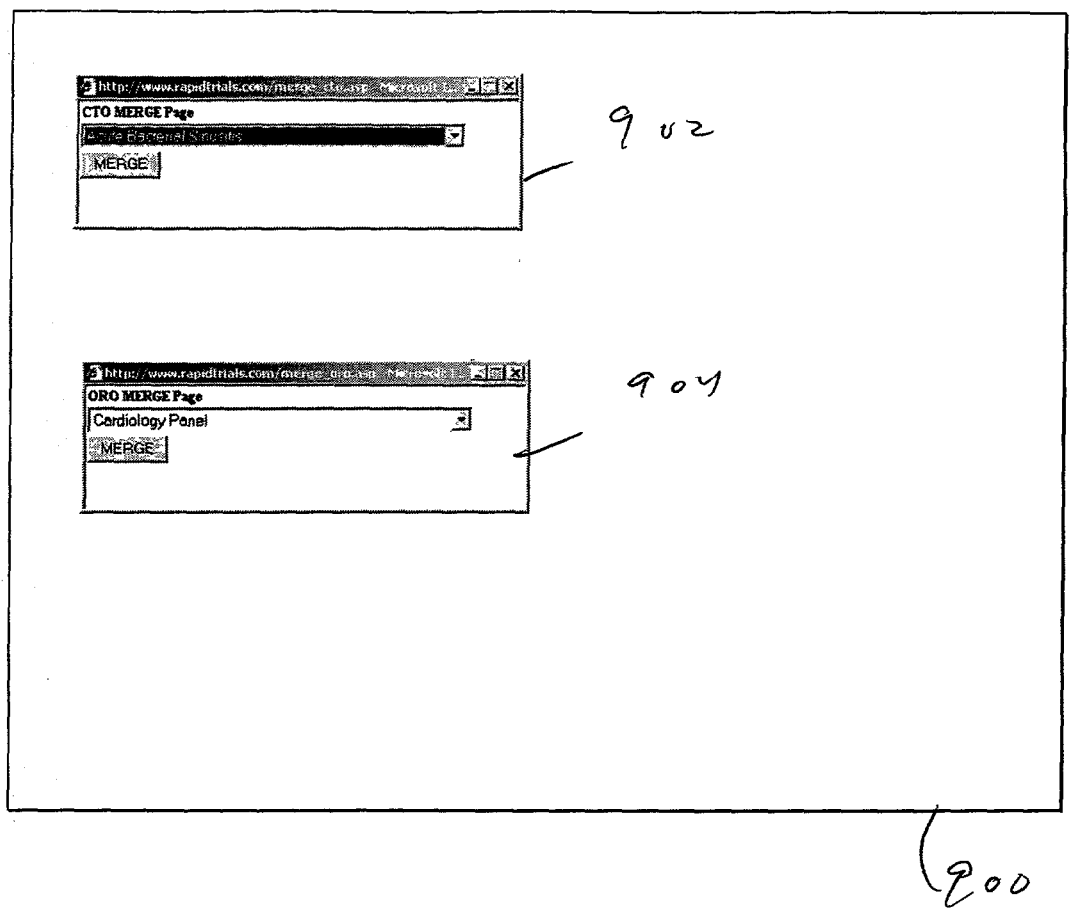
FIG. 9 shows a merge page.

Once the CTO or ORO is entered, the search results from FIG. 7 can be merged into the CTO or ORO. Once the button 728 or 730 is clicked, the merge page 902 or 904 in the merge area 900 of FIG. 9 appears. The user can select the Merge CTO or Merge ORO 902 or 904 and click the "Merge" button 906 or may cancel by closing the window. If the "Merge" button 906 is clicked, all of the selected search results from FIG. 7 are linked to the description of the CTO or ORO in the database. Checking for duplicate records is done automatically.

The physicians, organizations, or sites merged into the listing can be invited to consider the CTO or ORO. Since anyone found in the search results will have provided some contact information, the invitation can be made by e-mail, facsimile, or any other suitable channel.

Thus, the service (or, in an alternative embodiment, a sponsor of a CTO or ORO) can initiate contact with a physician, organization or site which may be suited to conduct that CTO or ORO, as described above with reference to FIG. 9. Either way, the questionnaire is completed and returned to the sponsor. The sponsor considers the questionnaire and can send a person to interview the physician or otherwise visit the organization or site at which the trial or other research would take place. A Web page can be provided to indicate the reasons why any particular physician, organization or site was accepted or declined. That Web page is accessible only by employees of the service or network members who have registered to use the system.

Once a physician, organization or site is selected to conduct the trial, data are collected for benchmarking. General (industry) benchmarks include the following: revenue per primary investigator per year, patients enrolled per number of coordinator FTE's, average revenue per patient, distribution of revenue by type, average enrollment as a percentage of goal, split of patient recruitment between in-house and advertised, average number of protocols per year, average number of years in clinical research, percentage of studies through third party, percentage of studies directly from CRO or sponsor, number of sponsors with which a particular physician, site or organization has worked, and number of CRO's with which a particular physician, site or organization has worked. Benchmarks specific to a particular study include the following: time to first patient enrolled, total patients enrolled after the first thirty days, actual enrollment as a percentage of the enrollment goal, per-patient budget, number of queries per patient, enrollment as a percentage of total patients screened, and elapsed time from notification of award of study to initiation visit. Data entered into the Web Form (Site Status Summary, or SSS) are used to compute the benchmarks specific to a particular study. Those data are collected on a per-protocol basis, are specific to that protocol and are not stored for future protocols. On the other hand, information collected in the profiles can be used to update the SQQ/PQQ.

Examples of Web pages for taking data associated with a particular study are shown in FIGS. 10 and 11 as 1000 and 1100, respectively. The page 1100 is only partially shown, since the data are taken not simply at the end of 30 days, but rather at the end of every 30-day interval until the end of the study; for instance, the page 1100 may ask for the number of patients screened after 720 days, etc. At the end of the study, data may be collected, such as the date of the study close-out visit and the number of queries generated.

The benchmarks are calculated automatically by the system. The more data inputted, the more an organization can access. They do not have to wait until the study is over until they can view benchmarks, but as soon as the relevant data are input the benchmark is viewable. Once all of the data are input and the study is concluded, or once the data currently available are input if benchmarking during the study is required, benchmarking can be performed using straightforward calculations on the data. Two examples of data outputs are shown; those skilled in the art will recognize that many other types of data outputs can be provided as needed.

Figure 12:
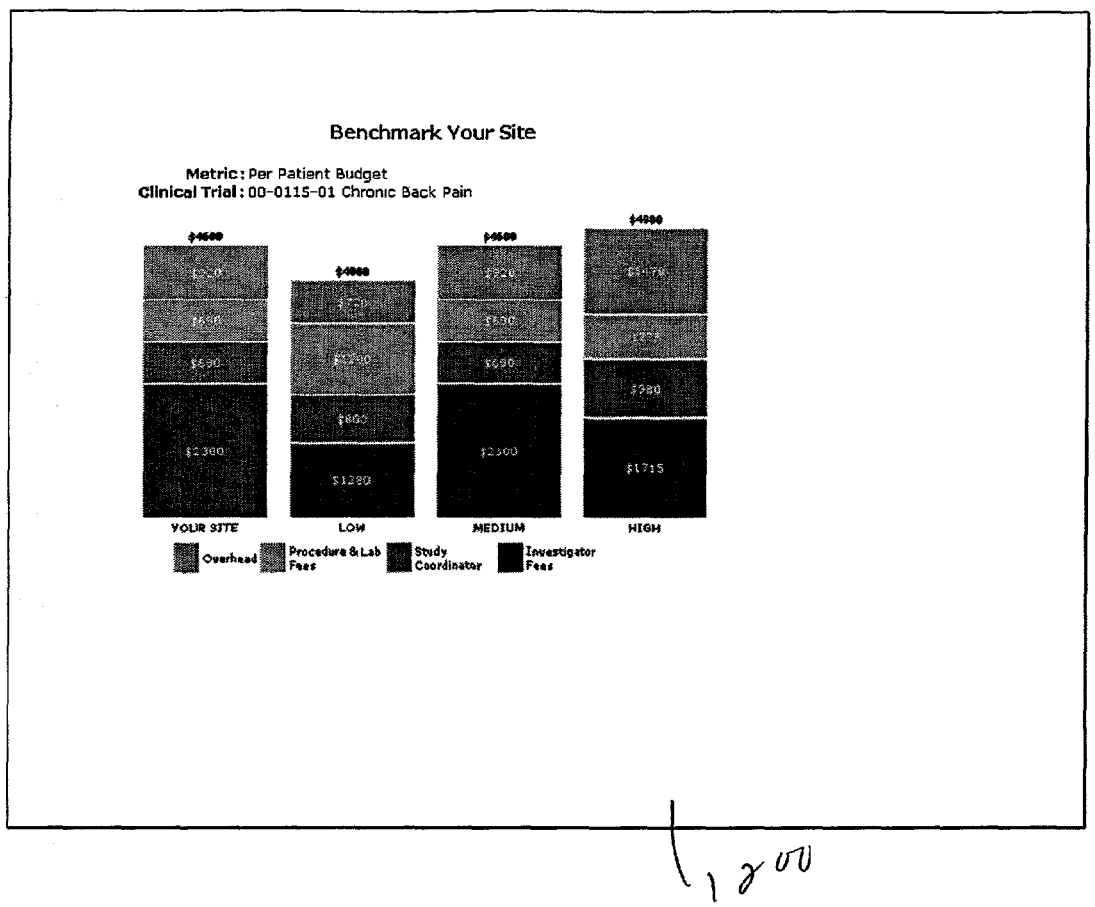
FIGS. 12 and 13 show pages used in displaying benchmark data.
Figure 13:
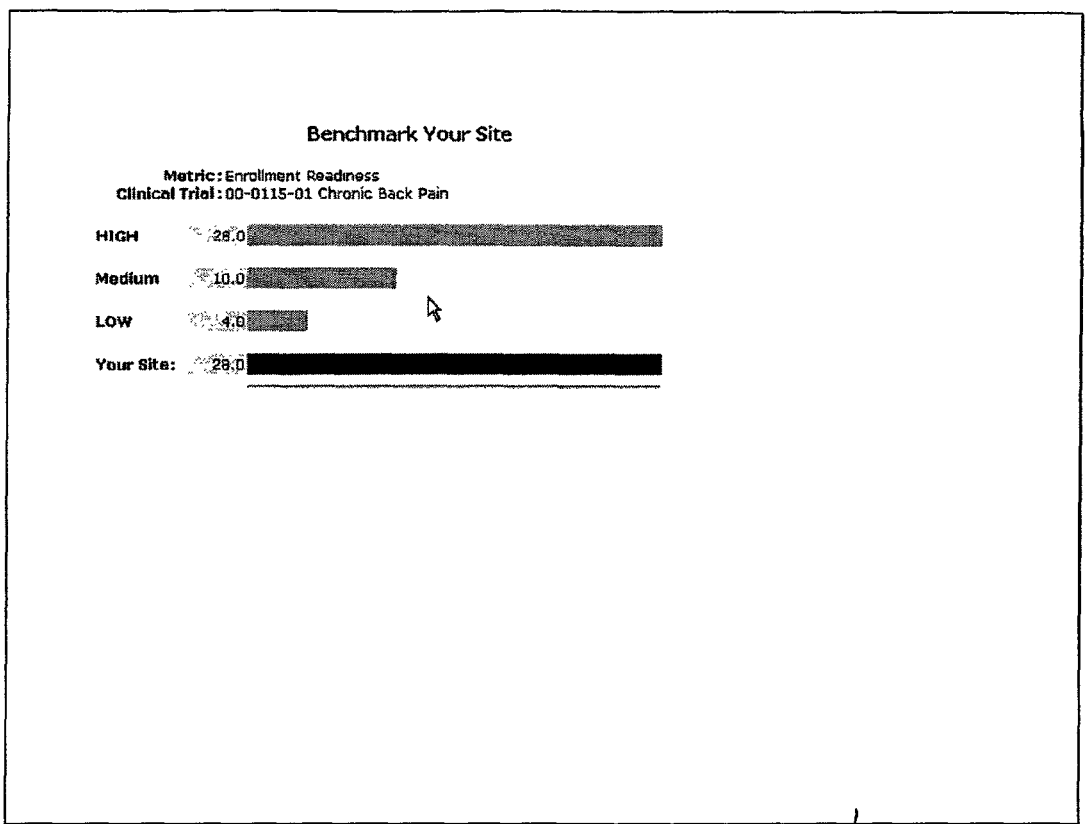

FIG. 12 shows a bar chart 1200 in which the total budget per patient is broken down into overhead, procedure and lab fees, the study coordinator, and the investigator fees. FIG. 13 shows a bar chart 1300 showing a particular benchmark by its value in the user's study compared to its high, low, and average values from among all organizations participating in the same opportunity monitored by the database server 114. The identities of the other organizations are not identified. Each of the bars of the bar chart 1300 can be broken up like the bar in the bar chart 1200.

The benchmarks can be displayed to the sponsor of the study, the physician, site or organization conducting the study, or both. Non-numerical information, such as the identities of the physicians involved in the study and information about them, can also be reported.

An enhancement to the service provides a customizable search page for the "study budget project" where physicians can search for a price range for their service. The search is intuitive enough to allow physicians to select predetermined criteria to focus their search. Physicians will also be able to download their study budget information in a standard template usable in a spreadsheet program (e.g., Microsoft Excel).

At step 1402, a study budget system is provided, which is a separate module from the service previously described. At step 1404, the user logs in. Members will pay a yearly license fee, billed monthly. Existing users will be able to retrieve their user name and password information by entering their e-mail address. If the system determines at step 1406 that the user is a new user, or is an existing member using the system for the first time, the user will be required to complete an activation form at step 1408. On confirmation of the user's credit card, the user will receive a welcome message and information about their subscription via e-mail.

At step 1410, the user will choose from standard study questions about that user's procedure type, which sets the parameters for the query. At step 1412, the user receives high, average, and low fees for the selected query.

At step 1414, a study budget template is provided in order to be populated with the user's information. The study budget template provides automatic calculations and a printable template. At step 1416, on completion of the template, the information is updated to the database.

While the disclosure set forth above is believed to provide an enabling disclosure of the present invention and a best mode for carrying out the present invention, an administrative-level user's guide will now be set forth for the sake of completeness. For ease of understanding, the user's guide is organized in tabular form.

| Question | Topic | Response |
|---|---|---|
| What happens when a site completes their application on-line or hard copy? | New Site Applications Completing Reference Check Information on Rapidtrials Activating a New Site | If it is completed on-line, E-mail Copy automatically goes to the service. The Site Recruiter then logs onto www.rapidtrials.com/orge.asp They select the organization name from the drop down list and hit EDIT They move using ALT + N or Next Page to the last page of the profile The last page lists the references They also list whether the references were: "outstanding" "Average" "Unfavorable" Once the reference checks are done, these are changed as appropriate The date the contract is signed is inputted into the first page, as well as some other contract information. Once the site is ready to be a member of the network the site recruiter goes to the first page of the organization profile, by going to www.rapidtrials.com/orge.asp, members admin, selecting the org name from the drop down and hitting EDIT Members admin page drop down list of organizations If the organization is in black it is an active member of the network, if the org is in blue or any other color you can check the status by going to Edit and looking at the status drop down halfway down page one of the organization profile. |

| Question | Topic | Response |
|---|---|---|
| | | Halfway down the first page is a status drop down. |
| | | The status is: |
| | | Active |
| | | Terminated |
| | | Contact |
| | | Hold |
| | | Pending |
| | | Inactive |
| | | The organization status is changed to Active. This automatically creates a second browser window with the User ID and Passwords for that organization. |
| | | You then select Export to XLS, and these can be printed out from XLS and faxed to the organization. |
| | | You then close the second browser window and select 'Save changes and Exit' |
| | | This organization is now an Active member of the network and has full access to the member's section. |
| How do I put a new clinical trial opportunity on Rapidtrials | Posting a New Clinical Trial Opportunity on Rapidtrials Creating a PCRS Tracking Number | The Project manager identifies a new CTO |
| | | Log on to Rapidtrials.com |
| | | This will take you to CTO Admin or www.rapidtrials.com/cto/asp |
| | | Click New |
| | | Enter the CTO name |
| | | Enter the Tracking Number |
| | | Enter if the CTO is recruiting Yes/No (When a CTO is no longer recruiting this must be changed to No) |
| | | Enter if the CTO is to be shown on the web Yes/No (When the CTO is no longer to be viewed on the web must be changed to NO) |
| | | Enter Project Manager Name |
| | | Enter which of the following are applicable (to be update, as information becomes available over time) |
| | | Sponsor |
| | | Sponsor contact Name |
| | | Sponsor Contract Name |
| | | CRO |
| | | CRO contact name |
| | | CRO contract name |
| | | Then select save |
| How do I create a CTO Online | Creating a Synopsis for a Clinical Trial (CTO) | Click CTO description |
| | | This is where you create the synopsis for the clinical trial |
| | | For those choices that appear in blue, click on the blue link, type in the text that is to appear under that link, click save and click return |
| | | Select Therapeutic Area and indication from the dropdown |
| | | Date CTO sent to sites |
| | | CTO Phase |
| | | Study design |
| | | Status- Proposed or awarded |
| | | Study Objective |
| | | Investigator specialty, up to three from dropdown |
| | | Clinical Experience, do they have to have experience or can they be trial naive |
| | | Is a certain number of past clinical trials necessary, indicate this here |
| | | IRB Utilization- Central or Local |
| | | Type of site, check all that apply |
| | | Is it Inpatient/Outpatient? |
| | | Key Inclusion Criteria |
| | | Key exclusion Criteria |
| | | Removal of patients from therapy |
| | | Length in enrollment in months |
| | | Note: This generates the correct amount of 30 day increments for the benchmarking |
| | | Expected enrollment |
| | | Duration of therapy |
| | | Number of patient visits |
| | | Investigator Meeting |
| | | Anticipated Start Date |
| | | Special request/equipment |
| | | Budget |
| | | There are then 5 extra criteria, which you can label and then enter text for |
| | | Click Save |
| How do I create a Site Qualification Questionnaire (SQQ) Online | Creating an SQQ Using the same template as a previously developed SQQ Creating Custom Questions | Click SQQ design |
| | | If there is another SQQ already created that you know is identical to the one you wish to create, or very similar so that you would change just one or two things- |
| | | Click Load SQQ pattern from another CTO |
| | | Select CTO Name and click OK |
| | | Say OK |
| | | This will create the same SQQ for your clinical trial |
| | | OR |
| | | To create a brand new SQQ |
| | | Click SQQ design |
| | | There will be a list of standard questions, these are questions that if they are completed on the profiles will pre fill for the Investigators |
| | | Select those you wish to delete |
| | | Note: The one that is blank is actually Board Certification |
| | | If you wish to create specialized questions, in addition to the standard questions, click Further Criteria |
| | | Click Simple Questions |
| | | A Question Interface appears |
| | | Let's use some examples: |
| | | How far away is the nearest airport? _____ in miles |
| | | Which of the following apply to your site? Small, Medium or Large |
| | | Check all that your site has ECG, Sleep Lab, Study Coord |
| | | What date is your next IRB meeting? |
| | | Using the Interface Label- |
| | | 1. Question One |
| | | Label = How far away is your site |
| | | After Label = miles |
| | | Question Type = Text box |
| | | Question Data Type = Text |
| | | Multiple Choices = |
| | | 2. Question Two |
| | | Label = Which of the following apply to your site? |
| | | After Label = |
| | | Question Type = Combo Box (only one answer allowed) |
| | | Question Data Type = Numeric |
| | | Multiple Choices = Small, Medium, Large |
| | | 3. Question Three |
| | | Label = Check all that your site has |
| | | After Label = |
| | | Question Type = Multiple Choices (allows for more than one answer) |
| | | Question Data Type = Numeric Multiple Choices = ECG, Sleep Lab, Study Coord |
| | | 4. Question Four |
| | | Label = What date is your next IRB meeting |
| | | After Label = |
| | | Question Type = Text box |
| | | Question Data Type = Date |
| | | Multiple Choices = |
| | | Then Click Save |
| | | This saves your question and it shows up under the Criteria Label |
| | | Continue clicking Simple Questions and then creating questions until you are done |

| Question | Topic | Response |
|---|---|---|
| | | To change any question you have already created, click the blue link and make your changes and click save |
| | | When you are done Click SQQ combination, this merges the standard questions and the special questions |
| | | Click re number, and then number the questions so that they appear in the correct order. |
| | | To delete a question click the delete box then save |
| | | To make further changes to the special questions click Edit further criteria and click on the blue links and make the change, click save and then SQQ combination |
| | | When you are satisfied with the order click Save |
| | | Then click Save Changes and Exit |
| TO send automatic emails to the orgs to inform them of a new CTO | | The project manager will provide with the new CTO a list of specialties who need to be informed about this trial |
| | | From CTO admin, click search, this appears above the matched site window |
| | | This will take you to the search page |
| | | Select enable- Membership Status |
| | | The choices are member, non-member, or all |
| | | Select member |
| | | Under Investigator specialty, click enable and choose the specialty from the drop down box |
| | | Note; The search by specialty is an AND search, not an OR search. So choose only one specialty at a time. |
| | | Click Find Physicians |
| | | At the bottom of the search results page, click select all |
| | | Review the list and those that you do not wish to inform of the clinical trial unselect them by clicking on the checkmark on the left-hand side so that the box is empty. |
| | | Then click merge CTO |
| | | Select the CTO name |
| | | Click Merge |
| | | This will dump the sites you selected into the matched window on the CTO admin page |
| | | Repeat with each specialty until completed |
| | | From CTO admin |
| | | Click Select All next to matched window |
| | | Click Send SQQ and description |
| | | This will create an email and fax list of all the matched organizations |
| | | To send the email click send mail all |
| | | One email is sent to each organization contact person that you identified, the email lists all the suitable investigators at that site. |
| TO add a doctor that has submitted for a clinical trial | | Go to CTO admin |
| | | Under CTO name drop down list, select the name and click Edit |
| | | OR |
| | | Enter tracking number on the top bar and click EDIT |
| | | IF |
| | | Doctor appears in matched window |
| | | Doctor does not appear in matched window |
| | | 1. Select his name by clicking on it |
| | | Click SSS |
| | | Then click EDIT under Update |
| | | Compete the first page: |
| | | Date of submission deadline |
| | | Date of submission |
| | | Date notified of submission |
| | | Note: This last field sends an automatic email to the site when it is completed. See attached email |
| | | Click Save changes and Exit |
| | | His status will now be Submitted pending selection |
| | | 2. From CTO admin halfway down |
| | | Select Org Name |
| | | Select Site |
| | | Select Physician |
| | | Click ADD |
| | | He will go into the top of the matched window |
| | | Follow above steps |
| To get a list of doctors submitted for a study (not including those whose status is not submitted) | | Go to responded window |
| | | Click on first name in the box |
| | | Click Shift |
| | | Click on last name in the box |
| | | Click Show Info |
| | | Print report |
| To remove a doctor from a trial | | Click on his name |
| | | Click remove |
| | | To view info for a doctor |
| | | Click his name |
| | | Click view info |
| | | Info is shown as: Name, Site, Org. Specialty, Tel #, Fax #, Status, Last Change |
| To update SSS | | Click his name |
| | | Click SSS |
| | | Click Edit under Update |
| | | To view SQQ |
| | | Click his name |
| | | Click SQQ |
| To add a new Sponsor | | Click New next to Sponsor |
| | | Enter Info |
| | | Click Save |
| | | Click Return |
| | | Same for Sponsor Contact, Sponsor Contract, CRO, CRO Contact, and CRO Contract |
| | Search Page | Every criteria you enable limits your search |
| | | It is a wild card to search: |
| | | To search for Bill Jones, enable physician name and enter |
| | | Bill |
| | | Jones |
| | | Bi |
| | | Ll |
| | | Jo |
| | | Nes |
| | | Etc |
| | | Click find physicians to get results |
| | | Results are shown as Org, Site, Physician, Phone, Fax, Specialty, Status (member/non-member), CTO, ORO |
| | | The results can be sorted by any of the column headings, simply click on them |
| | | Clicking on the physician's name takes you to his profile |
| | | Clicking on the site name takes you to the site profile |
| | | Clicking on the org name takes you to the organization profile |
| To transfer a doctor | | If a doctor moves from one organization, or more likely someone entered him in the wrong organization profile |
| | | Search for the physicians |
| | | From the results page select doctor to be transferred |
| | | Member Admin Page |
| | | Organization Level |
| | | To create a new org, click new |
| | | To edit an existing org, select name from drop down list and click edit |
| | | Click Transfer |

| Question | Topic | Response |
|---|---|---|
| | | Select Org and Site he is to be transferred to |
| | | Click Transfer |
| | | To view (in read only mode) an existing org, select name from drop down list and click show |
| | | To view the sites for that org, select site name from drop down and click site |
| | | Site Level |
| | | To create a new site, click new |
| | | To edit an existing site, select name from drop down list and click edit |
| | | To view (in read only mode) an existing site, select name from dropdown list and click show |
| | | To view the members for that site, select site name from drop down and click members |
| | | To view the SSS for a site (all the trials that they are linked with) click SSS |
| | | To delete a site, select the site name from the drop down and click delete |
| | | Members Level |
| | | To create a new member, click new |
| | | To edit an existing member, select name from drop down lists and click edit |
| | | To view (in read only mode) an existing member, select name from dropdown list and click show |
| | | To view the SSS for member (all the trials that they are linked with) click SSS |
| | | To delete a member, select the member name from the drop down and click delete |
| | | Please Note |
| | | If you change the organization name at the organization level, the site level and the member level DOES NOT AUTOMATICALLY CHANGE. |
| | | You must click Site and Member again to ensure the information you are looking at is relevant to the site that you are viewing |
| | | To view the SSS for and org (all the trials that they are linked with) click SSS |
| | | To delete an org, select the org name from the drop down and click delete |
| | | Mini search for CTO Issues |
| | | Results are always shown as CTO Number, Org Name, Site Name, Physician, Specialty, Phone, Fax, Sponsor/CRO, Status, Last Change, Access to SSS |
| SSS Search Criteria | | You can search by |
| | | Tracking Number |
| | | Organization Name |
| | | Site Name |
| | | Physician Name |
| | | The more information you enter the more limited your search |
| | | After you enter the search criteria, click find |
| | | To get to CTO admin, click CTO |
| | | To reset search criteria, click reset |
| | Passwords | Click Passwords Link |
| | | Select the organization that you want to get passwords for |
| | | Click Update |
| | | Make changes and to save click update |
| | | To print, click print |
| | | To export to XLS, click export to XLS |
| | Tracking of Web Site Changes | These are tracked by |
| | | SSS changes |
| | | SQQ changes |
| | | Profile changes |
| | | It tracks- Tracking number, Physician, Site, Org, Date and Time of change, Location of change (form name and page) |
| | Physician History | View which CTO have been sent to a physician and whether they responded (yes or no) |
| | | Search by name, site, organization or institution (for ORO doctors) |
| | | Limit as much as you want, more info, more limited search, another wild card search |
| | | Hit Find |
| | | Then select which physician and click View |
| | | History |
| | | History shown as CTOs offered responded Yes/No |
| | | OROs offered responded Yes/No |
| | Sponsor Requests Results of tell us about your needs Marketer Requests Results of See what we can do for you | |

Various other enhancements can be made to the present invention. They will now be set forth.

| Functionality | Description |
|---|---|
| Best Practices Across All Sites Benchmarked | Extension of the benchmarking capability, this would be accessible to members. Based on benchmarking metrics, those sites with the best practices will be identified by the service, contacted and interviewed on how they obtained the results in this trial. This information will be shared confidentially with other sites in the same protocol. This will promote information exchange amongst sites, help research naive sites, or poorer performing sites to achieve better results on studies, and identify problems before a study closeout situation occurs |
| Secure Bulletin Board | Each clinical trial listed on Rapidtrials and whose status is on-going will have a one (1) way (from the service outboard) Bulletin Board where sponsors can post information about a study including Q&A type information In addition, Sponsor project managers can use the bulletin Board to share information about the study on a on-going basis |
| Rapid Budget | Separate Web Module accessible from the current website (rapidtrials.com). Members pay a yearly fee, billed monthly. They can apply for membership via the website (rapidtrials.com), with payment accepted via credit card. A new user will be required to complete an activation form; this will collect basic data on the physician and his organization. The module will ask them |

-continued

| Functionality | Description |
|---|---|
| | questions about the type of study they wish to budget for and which procedures are involved. Users receive a high, average, low, and your site (which allows them to view what they charged for the procedure the last time they used the system). The system then asks them to choose a price for each procedure, this feeds into a basic per patient clinical trial specific study budget template which when they have completed choosing their ranges they can print the complete budget worksheet from the website. This information then updates the underlying sequel table, so it will be available to be used in the calculation for the next user. |
| RapidTraining | Current Training Program owned by the service is for Novice Sites and or as a refresher course for experienced sites. Currently we have the program on CD and will Migrate the CD based training program to the Web as a standalone serviced |
| Rapid Meeting | Investigator CD platform currently exists. Will be migrated to the Web. |
| Rapidpatient Recruitment | This will be a guide Clinical Research sites in selecting strategies and tactics to aid in the clinical trial patient recruitment and retention activities. Based upon a users description of the patient recruitment and retention objectives they are attempting to support, the Rapidtrials web module will suggest appropriate tactics to support the objectives. This module will also include IRB/FDA regulations governing patient recruitment advertising and recruitment guidelines. This module of the Rapidtrials website will be a portal for ordering mugs, t-shirts, ads, media buying, plaques and other promotional items through the service to enhance patient recruitment and retention in clinical trials. A catalog of items, which are IRB/FDA compliant that they can order through us. |
| Rapid Assessment | A Rapidtrials web module that uses a psycho-behavioral assessment (similar to Myers Briggs) that has been validated by the service using historical performance and behavioral assessment response correlation's to identify sites with a high probability of succeeding in clinical trials. Investigators and coordinators will complete this behavioral assessment on-line as a predictive tool for the practice of future success in clinical trials. Gaps in attributes will be identified for Sites as a means of guiding them in clinical research program recruitment. For sponsors involved in site selection, or preparing to invest in site development it will give them another performance indicator prior to selecting sites to participate in a clinical trial. |
| Industry Benchmarking | Generated by data entered into members organization, site and Investigator profiles, these benchmarks will be displayed by Type of Organization (I.e. solo practice, SMO etc): Total number of protocols per year, Total grant value per protocol, total number of patients enrolled in a clinical trial/year, total number of Study coordinators, total number of sites doing research, Total number of Patients per study coordinator FTE's, Average number of Patients per year, Number of Physicians, Number of PI's, Overhead as a percentage of total per patient budget, Study Coordinator costs as a percentage of Total per patient budget, Investigator Fees as a percentage of total per patient budget, Procedure, lab fees as a percentage of total per patient budget, total number of sponsors worked for/year, Total number of CROs/year, Actual Enrollment/Enrollment Goal. |
| Site Capabilities Assessment Data Capture and Reporting | Data capture approved by field based consultants to gather information on sites developing research programs or preparing to participate in clinical trial. Migration of proprietary data capture tools to the web. |
| Site Operations Specialists Site Specialists Site Development eWorkbook | Data capture pages used by field based consultants to gather information on sites developing research programs or preparing to participate in clinical sites developing research programs or preparing to participate in clinical trial. Migration of proprietary data capture tools to the web. This is the same as the above. |
| Site Operations Specialists Site Management eWorkbook | Data Capture Pages, tools and presentations to use in preparing for and monitoring site performance on a clinical trial. Migration of Proprietary Data Capture tools to the web |

While a preferred embodiment of the present invention has been set forth in detail, those skilled in the art who have reviewed the present disclosure will readily appreciate that other embodiments can be realized within the scope of the present invention. For example, the utility of the invention is not limited to the medical field. Also, any benchmarks can be calculated, in which case the forms for collecting the data are modified accordingly. Further, the benchmarks can be displayed as text, as any suitable chart, or as a combination of the two. In addition, either the Web server or the database server can incorporate the ability to handle payments from one participant to another, as well as from participants to the company operating the servers. Moreover, any mention of a specific software package (e.g., Microsoft Excel) should be construed as illustrative rather than limiting. Therefore, the present invention should be construed as limited only by the appended claims.

What is claimed is:

1. A system for collecting metrics and calculating and communicating benchmarking information concerning the conduct of a clinical research trial among a plurality of research sites and a plurality of investigators participating in the conduct of said clinical research trial, the system comprising:

a database server for (i) providing a user interface for capturing and displaying investigator and research site metrics for a plurality of research sites and the plurality of investigators who are participating in said clinical research trial, such metrics including at least one of time to first patient enrolled, total patients enrolled after the first 30 days, actual enrollment as a percentage of the enrollment goal, enrollment rate, screen failure rate, completion rate, per-patient budget, number of queries per patient, enrollment as a percentage of patients screened, and elapsed time from irb submission to irb approval, (ii) storing said collected investigator and research site metrics useful at least for calculating benchmarking information regarding the conduct of said clinical research trial; and (iii) automatically calculating said benchmarking information for each of said plurality of investigators and each of said plurality of clinical research sites participating in said clinical research trial using said collected investigator and research site metrics for said clinical research trial, said benchmarking information comprising information comparing each of said plurality of clinical research sites and each of said plurality of investigators to all clinical research sites and all investigators participating in said clinical research trial; and a communication server, in communication with said database server, for providing a user interface for communicating some or all of said calculated benchmarking information in real time to one or more of said plurality of investigators and one or more of said plurality of clinical research sites, said calculated benchmarking information being viewable immediately after said investigator and research site metrics are received by said database server.

2. The system of claim 1, wherein the benchmarking information comprises investigator and research metrics continually received by said database server during the clinical research trial.

3. The system of claim 2, wherein the benchmarking information further comprises investigator and research site metrics received by said database server at a beginning of the clinical research trial, throughout the clinical trial, and at an end of the clinical research trial, aggregated for viewing by a sponsor or representatives of a sponsor.

4. The system of claim 2, wherein the benchmarking information further comprises investigator and research site metrics received by said database server at a beginning of the clinical research trial, throughout the clinical trial, and at an end of the clinical research trial.

5. The system of claim 2, wherein the benchmarking information comprises comprise a comparison between the benchmarks of a variety of investigator and research site metrics for the clinical research trial and the benchmarks for other clinical research sites involved in the same clinical research trial.

6. A method for collecting metrics, and calculating and communicating benchmarking information concerning conduct of a clinical research trial among a plurality of research sites and a plurality of investigators participating in the conduct of said clinical research trial, the method comprising the steps of:

(a) providing a user interface for capturing and displaying investigator and research site metrics on a database server for a plurality of research sites and the plurality of investigators who are participating in said clinical research trial, such metrics including at least one of time to first patient enrolled, total patients enrolled after the first 30 days, actual enrollment as a percentage of the enrollment goal, enrollment rate, screen failure rate, completion rate, per-patient budget, number of queries per patient, enrollment as a percentage of patients screened, and elapsed time from irb submission to irb approval;

(b) storing on said database server said collected investigator and research site metrics useful at least for calculating benchmarking information regarding the conduct of said clinical research trial;

(c) automatically calculating on said database server said benchmarking information for each of said plurality of investigators and each of said plurality of clinical research sites participating in said clinical research trial using said collected investigator and research site metrics for said clinical research trial, said benchmarking information comprising information comparing each of said plurality of clinical research sites and each of said plurality of investigators to all clinical research sites and all investigators participating in said clinical research trial; and (d) providing a user interface for communicating some or all of said calculated benchmarking information in real time to one or more of said plurality of investigators and one or more of said plurality of clinical research sites, said calculated benchmarking information being viewable immediately after said collected investigator and research site metrics are received by said database server.

7. The method of claim 6, wherein said collected investigator and research site metrics stored on said database server comprise metrics received by said database server at multiple times during the clinical research trial in order to update the calculated benchmarking information.

8. The method of claim 7, wherein said collected investigator and research site metrics stored on said database server comprise metrics received at regular time intervals during the clinical research trial updated at any time once the clinical research trial has begun, and wherein updated benchmarking information is viewable automatically as the benchmarking information is updated throughout the duration of the clinical research trial.

9. The method of claim 8, wherein said collected investigator and research site metrics stored on said database server further comprise metrics received at a beginning of the clinical research trial, intervals throughout the clinical research trial, and at an end of the clinical research trial.

10. The method of claim 9, wherein the benchmarking information comprises benchmarks for the regular time intervals.

11. The method of claim 6, wherein the benchmarking information comprises a comparison between the benchmarks of a variety of collected investigator and research site metrics for the clinical research trial of one clinical research site to other clinical research sites involved in the same clinical research trial.

12. The method of claim 8, wherein said collected investigator and research site metrics stored on said database server comprise metrics received at a beginning of the clinical research trial, intervals throughout the clinical research trial, and at an end of the clinical research trial, aggregated for viewing by a sponsor or representatives of a sponsor.

* * * * *